US006395306B1

(12) United States Patent
Cui et al.

(10) Patent No.: US 6,395,306 B1
(45) Date of Patent: May 28, 2002

(54) BEE VENOM PROTEIN AND GENE ENCODING SAME

(75) Inventors: Xiangmin Cui, Cupertino; Yuefeng Lu, San Carlos, both of CA (US)

(73) Assignee: Pan Pacific Pharmaceuticals, Inc., Lincoln, RI (US)

( * ) Notice: Subject to any disclaimer, the term of this patent is extended or adjusted under 35 U.S.C. 154(b) by 0 days.

(21) Appl. No.: 09/394,630

(22) Filed: Sep. 13, 1999

Related U.S. Application Data

(60) Provisional application No. 60/100,172, filed on Sep. 14, 1998.

(51) Int. Cl.$^7$ .................... A61K 35/64; A61K 35/24; C12P 21/06; C12P 2/02; C12N 15/00
(52) U.S. Cl. .................. 424/539; 424/537; 435/69.1; 435/69.5; 435/320.1; 435/325; 536/23.1
(58) Field of Search .................. 435/69.1, 69.5, 435/320.1, 325; 424/537, 539; 536/23.1

(56) References Cited

U.S. PATENT DOCUMENTS 3,856,936 A 12/1974 Vick et al.

FOREIGN PATENT DOCUMENTS

WO WO 98/56400 12/1998

OTHER PUBLICATIONS

Banks, et al., "Chemistry and Pharmacology of Honey–bee Venom" in *Venoms of the Hymenoptera: Biochemical, Pharmacological and Behavioral Aspects* (Piek, T., Ed.), Academic Press, chap. 7, pp. 397–398 (1986).
Shipolini, Rudolf A., "Biochemistry of Bee Venom" in *Handbook of Natural Toxins, Allergans and Other Invertebrate Venoms*, (Tu, Anthony T., Ed.) Marcel Dekker, Inc., vol. 2, pp. 58–59 (1984).
Kim, Christopher M., M.D., Honey Bee Venom Therapy for Arthritis (RA, OA)Fibromyositis (FM) and Peripheral Neuritis (PN), *The Journal of the Korean Pain Research Society*, Dec., 1991, vol. 1, No. 1, pp. 55–65.
Product Information on Nectar Ease, http://www.huggers.com/NectarEase/productinfo.htm, Jun. 15, 1998, pp. 1–8.
Freeman, Karen, Charles Mraz, 94, Advocate of Therapeutic Bee Sting, Dies, *The New York Times, Sunday National Desk*, Sep. 19, 1999, (as found at http://nytimes.qpass.com pp. 1–4).
Shkenderov, Stefan and Koburova, Krasimira; Adolapin—A Newly Isolated Analgetic And Anti–Inflammatoy Polypeptide From Bee Venom, *Toxicon*, Great Britain, 1982, vol. 20, No. 1, pp. 317–321.
Koburova, K. L.; Michailova, S. G. and Shkenderov, S. V.; Further Investigation on the Antiinflammatory Properties of Adolapin—Bee Venom Polypeptide, *Bulgarian Academy of Sciences*, 1985, vol. 8, No. 2, pp. 50–55.
Koburova, K.; Mihailova, S. and Shkenderov, S.; The Antipyretic Effect Of One Polypeptide From The Bee Poison—Adolapin, *Eksp Med Morfol*, 1984, 23(3) pp. 143–148.

Cohen, A., M.D.; Dubbs, A. W., M.D.; Pearah, J. B., M.D.; and Best, C. J., M.D.; Bee Venom in the Treatment of Chronic Arthritis, A Comparative Study, *The Pennsylvania Medical Journal*, Jun., 1942, vol. 45, No. 9, pp. 957–959.
Marz, Charles, Bee Venom for Arthritis—An Update, *American Bee Journal*, Feb., 1982, pp. 121–123.
Shkenderov, S., New Pharmacobiochemical Data on the Anti–Inflammatory Effect of Bee Venom, in *Animal, Plant, and Microbial Toxins*, 1976, vol. 2, pp. 319–336.
Hollander, J. L., M.D., Bee Venom In The Treatment Of Chronic Arthritis, *The American Journal OF The Medical Sciences*, Jun., 1941, vol. 201, No. 6, pp. 796–801.
Guyton, F. E., Bee Sting Therapy for Arthritis and Neuritis, *Journal of Economic Entomology*, 1947, vol. 40, pp. 469–472.
Kroner, J., M.D.; Lintz, R.M., M.D.; Tyndall, M., M.D., Andersen, L., M. D.; and Nicholls, E. E., M.D.; The Treatment of Rheumatoid arthritis With An Injectable Form Of Bee Venom, *Annals Of Intenal Medicine*, Jan., 1938, vol. 11, No. 7, pp. 1077–1083.
Chang, Yi–Han and Bliven, Marcia L.; Anti–Arthritic Effect of Bee Venom, *Agents and Actions*, 1979, vol. 9/2, pp. 205–211.
Billingham, M. E. J.; Morley, J.; Hanson, J. M.; Shipolini, R. A.; and Vernon, C. A.; An Anti–Inflammatory Peptide from Bee Venom, *Nature*, Sep. 21, 1973, vol. 245, pp. 163–164.
Zurier, R. B.; Mitnick, H.; Bloomgarden, D.; and Weissmann, G.; Effect of Bee Venom on Experimental Arthritis, *Annal of the Rheumatic Diseases*, 1973, vol. 32, pp. 466–470.
Vick, J. A.; Warren, G. B.; and Brooks, R. B., Jr.; The Effect Of Treatment With Whole Bee Venom On Cage Activity And Plasma Cortisol In The Arthritic Dog, *Inflammation*, 1975–1976, vol. 1, No. 2, pp. 167–174.
Somerfield, S. D.; Stach, J. L.; Mraz, D.; Gervais, F.; and Skamene, E.; Bee Venom Inhibits Superoxide Production By Human Neutrophils, *Inflammation*, 1984, vol. 8, No. 4, pp. 385–391.
Shkenderov, S.; A Protease Inhibitor In Bee Venom (Identification, Partial Purification and some Properties), *FEBS Letters*, Jul. 1973, vol. 33, No. 3, pp. 343–347.
Hyre, H. M. and Smith, R. A.; Immunological Effects Of Honey Bee (APIS Mellifera) Venom Using BALB/c Mice, *Toxicon*, 1986, vol. 24, No. 5, pp. 435–440.

(List continued on next page.)

*Primary Examiner*—Jeffrey Stucker
*Assistant Examiner*—Jegatheesan Seharaseyon
(74) *Attorney, Agent, or Firm*—Townsend and Townsend and Crew LLP; Scott Ausenhus

(57) ABSTRACT

The invention provides a novel protein, PX3.101, which can be isolated from honey bee venom, antibodies against the polypeptide and nucleic acids encoding PX3.101 and fragments thereof. The invention also provides pharmaceutical compositions based upon PX3.101 polypeptide and methods for using same in the treatment of various diseases, including various inflammatory diseases such as rheumatoid arthritis.

24 Claims, 9 Drawing Sheets

OTHER PUBLICATIONS

Eiseman, J. L.; von Bredow, J. and Alvares, A.P.; Effect Of Honeybee (Apis Mellifera) Venom On The Course Of Adjuvant–Induced Arthritis And Depression Of Drug Metabolism In The Rat, *Biochemical Pharmacology*, 1982, vol. 31, No. 6, pp. 1139–1146.

Beck, Bodog F., M. D.; Bee Venom Therapy (Bee Venom, Its Nature, and Its Effect on Arthritic and Rheumatoid Conditions), D. Appleton–Century Company, Inc., New York and London, 1935, pp. 150–197.

Broadman, Joseph, M.D., Bee Venom (The Natural Curative For Arthritis And Rheumatism), G. P. Putnam's Sons, New York, 1962, pp. 13–18.

Broadman, Joseph, M.D., Bee Venom (The Natural Curative For Arthritis And Rheumatism), G. P. Putnam's Sons, New York, 1962, pp. 28–50.

McCulloch, Michael, L.Ac., Frequently Asked Questions about Apitherapy, http://www.apitherapy.org/aas/faq.html., 1997, pp. 1–9.

Frei, Erich; Schuh, Reinhard; Baumgartner, Stefan; Burri, Maya; Noll, Markus; Jurgens, Gerd; Seifert, Eveline; Nauber, Ulrich and Jackie, Herbert; Molecular characterization of spalt, a homoeotic gene required for head and tail development in the Drosophia embryo, *The EMBO Journal*, 1988, vol. 7, No. 1, pp. 197–204.

```
ATTCACAGTGCAACGTAAGTTCTTTTCTTCTTTTTTTCGAAAAAACAACTTT                                    55

GTTTGAGAAGAAACAAACATGTCTCGTCTTGGTTCTTGCCTCCTTCCTCTTTG                                  109
                M   S   R   L   V   L   A   S   F   L   L   L                          12

GCAATTTTCTCCATGCTCTTGTTGGTGGAGGATTTGGAGGATTTGGAGGA                                     163
 A   I   F   S   M   L   V   G   G   F   G   G   F   G   G   G                         30

CTTGGAGGACGTGGTAAATGTCCAAGCAATGAGATCTTCAGTAGATGCGATGGA                                 217
 L   G   G   R   G   K   C   P   S   N   E   I   F   S   R   C   D   G                 48

CGGTGCCAACGTTTTTGCCCCAATGTTGTTCCTAAACCTTTATGCATCAAGATA                                 271
 R   C   Q   R   F   C   P   N   V   V   P   K   P   L   C   I   K   I                 66

TGTGCACCAGGATGTGTATGAGACTTGGTTATTAAGGAATAAAAAGAAGTA                                    325
 C   A   P   G   C   V   C   R   L   G   Y   L   R   N   K   K   K   V                 84

TGCCGTTCCGCGATCTAAATGCGGATGACTTTTATAATTATTCATGATTATTTT                                 379
 C   V   P   R   S   K   C   G   *                                                     92

ATGATTGTTTAACAATTATTGTATTGTATTTTATCATTCATAAAAATTGTTATG                                 433

TTATTATTTTATCAGTAAAAAAAAAAAAAAAAAAAAA                                                  472
```

FIG. 3A.

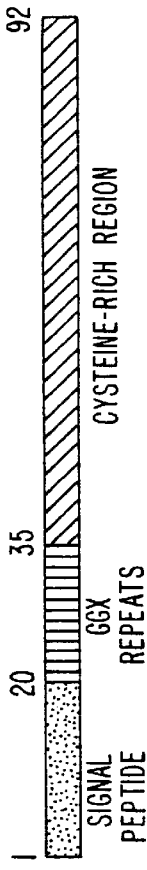

FIG. 3B.

| PX3.101 | | 92 aa |
| AC006093.12 | | 90 aa |
| CAA98455 | | 245 aa |
| AAB65990 | | 166 aa |
| AAA92314 | | 135 aa |
| AAA92313 | | 137 aa |
| AAB09171 | | 98 aa |

SIGNAL PEPTIDE

GGX REPEATS

CYSTEINE-RICH REGION aa   AMINO ACID

SEQUENCE LISTING

<160> NUMBER OF SEQ ID NOS: 22

<210> SEQ ID NO 1
<211> LENGTH: 472
<212> TYPE: DNA

```
<213> ORGANISM: Apis mellifera
<220> FEATURE:
<221> NAME/KEY: CDS
<222> LOCATION: (74)..(352)
<223> OTHER INFORMATION: honey bee venom PX3.101 protein

<400> SEQUENCE: 1
attcacagtg caacgtaagt tcttttcttc ttttttttt cgaaaaaaca actttgtttg        60
agaagaacaa aac atg tct cgt ctg gtt ctt gcc tcc ttc ctt ctt ttg        109
            Met Ser Arg Leu Val Leu Ala Ser Phe Leu Leu Leu
              1               5                  10 gca att ttc tcc atg ctt gtt gga gga ttt gga gga ttt gga gga ttt        157
Ala Ile Phe Ser Met Leu Val Gly Gly Phe Gly Gly Phe Gly Gly Phe
         15                  20                  25 gga gga ctt gga gga cgt ggt aaa tgt cca agc aat gag atc ttc agt        205
Gly Gly Leu Gly Gly Arg Gly Lys Cys Pro Ser Asn Glu Ile Phe Ser
     30                  35                  40 aga tgc gat gga cgg tgc caa cgt ttt tgc ccc aat gtt gtt cct aaa        253
Arg Cys Asp Gly Arg Cys Gln Arg Phe Cys Pro Asn Val Val Pro Lys
 45                  50                  55                  60 cct tta tgc atc aag ata tgt gca cca gga tgt gta tgt aga ctt ggt        301
Pro Leu Cys Ile Lys Ile Cys Ala Pro Gly Cys Val Cys Arg Leu Gly
                 65                  70                  75 tat tta agg aat aaa aag aag gta tgc gtt ccg cga tct aaa tgc gga        349
Tyr Leu Arg Asn Lys Lys Lys Val Cys Val Pro Arg Ser Lys Cys Gly
             80                  85                  90 tgacttttat aattatttca tgattatttt atgattgttt aacaattatt gtattgtatt      409
ttatcattca taaaaattgt tatgttatta ttttatcagt aaaaaaaaaa aaaaaaaaa       469 aaa                                                                   472

<210> SEQ ID NO 2
<211> LENGTH: 92
<212> TYPE: PRT
<213> ORGANISM: Apis mellifera

<400> SEQUENCE: 2

Met Ser Arg Leu Val Leu Ala Ser Phe Leu Leu Leu Ala Ile Phe Ser
  1               5                  10                  15

Met Leu Val Gly Gly Phe Gly Gly Phe Gly Gly Phe Gly Gly Leu Gly
                 20                  25                  30

Gly Arg Gly Lys Cys Pro Ser Asn Glu Ile Phe Ser Arg Cys Asp Gly
             35                  40                  45

Arg Cys Gln Arg Phe Cys Pro Asn Val Val Pro Lys Pro Leu Cys Ile
         50                  55                  60

Lys Ile Cys Ala Pro Gly Cys Val Cys Arg Leu Gly Tyr Leu Arg Asn
 65                  70                  75                  80

Lys Lys Lys Val Cys Val Pro Arg Ser Lys Cys Gly
                 85                  90

<210> SEQ ID NO 3
<211> LENGTH: 26
<212> TYPE: DNA
<213> ORGANISM: Artificial Sequence
<220> FEATURE:
<223> OTHER INFORMATION: Description of Artificial Sequence:forward
      primer ASEQ10

<400> SEQUENCE: 3
aaggatccac agtgcaacgt aagttc                                           26
```

<210> SEQ ID NO 4
<211> LENGTH: 55
<212> TYPE: DNA
<213> ORGANISM: Artificial Sequence
<220> FEATURE:
<223> OTHER INFORMATION: Description of Artificial Sequence:forward
      primer ASEQ11

<400> SEQUENCE: 4
aaggatccgg aggatttgga ggatttggag gatttggagg acttggagga cgtgg          55

<210> SEQ ID NO 5
<211> LENGTH: 17
<212> TYPE: DNA
<213> ORGANISM: Artificial Sequence
<220> FEATURE:
<223> OTHER INFORMATION: Description of Artificial Sequence:reverse
      primer ASEQ13

<400> SEQUENCE: 5
actgataaaa taataac                                                    17

<210> SEQ ID NO 6
<211> LENGTH: 16
<212> TYPE: DNA
<213> ORGANISM: Artificial Sequence
<220> FEATURE:
<223> OTHER INFORMATION: Description of Artificial Sequence:reverse
      primer ASEQ14

<400> SEQUENCE: 6
atgaatgata aaatac                                                     16

<210> SEQ ID NO 7
<211> LENGTH: 17
<212> TYPE: DNA
<213> ORGANISM: Artificial Sequence
<220> FEATURE:
<223> OTHER INFORMATION: Description of Artificial Sequence:reverse
      primer ASEQ15

<400> SEQUENCE: 7
ttataaaagt catccgc                                                    17

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence:degenerate
      oligonucleotide primer
<221> NAME/KEY: modified_base
<222> LOCATION: (23)
<223> OTHER INFORMATION: n = g, a, c or t

<400> SEQUENCE: 8
atggatccaa ygarathtty wsnag                                           25

<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence:amino acid
      sequence obtained from protein sequencing

<400> SEQUENCE: 9

```
Asn Glu Ile Phe Ser Arg
  1               5
```

```
<210> SEQ ID NO 10
<211> LENGTH: 28
<212> TYPE: DNA
<213> ORGANISM: Artificial Sequence
<220> FEATURE:
<223> OTHER INFORMATION: Description of Artificial Sequence:Oligo(dT)

<400> SEQUENCE: 10
ttgcggccgc tttttttttt tttttttt                                      28
```

```
<210> SEQ ID NO 11
<211> LENGTH: 8
<212> TYPE: PRT
<213> ORGANISM: Artificial Sequence
<220> FEATURE:
<223> OTHER INFORMATION: Description of Artificial Sequence:residues
      38-45 of SEQ ID NO:2 obtained through protein
      sequencing; peptide fragment #75 from in-gel
      trypsin digestion

<400> SEQUENCE: 11

Pro Ser Asn Glu Ile Phe Ser Arg
  1               5
```

```
<210> SEQ ID NO 12
<211> LENGTH: 11
<212> TYPE: PRT
<213> ORGANISM: Artificial Sequence
<220> FEATURE:
<223> OTHER INFORMATION: Description of Artificial Sequence:residues
      24-34 of SEQ ID NO:2 obtained through protein sequencing

<400> SEQUENCE: 12

Gly Phe Gly Gly Phe Gly Gly Leu Gly Gly Arg
  1               5                  10
```

```
<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence:residues
      84-88 of SEQ ID NO:2 obtained through protein sequencing

<400> SEQUENCE: 13

Val Cys Val Pro Arg
  1               5
```

```
<210> SEQ ID NO 14
<211> LENGTH: 6
<212> TYPE: PRT
<213> ORGANISM: Artificial Sequence
<220> FEATURE:
<223> OTHER INFORMATION: Description of Artificial Sequence:residues
      55-60 of SEQ ID NO:2 obtained through protein sequencing

<400> SEQUENCE: 14

Pro Asn Val Val Pro Lys
  1               5
```

```
<210> SEQ ID NO 15
<211> LENGTH: 13
<212> TYPE: DNA
<213> ORGANISM: Artificial Sequence
<220> FEATURE:
```

```
<223> OTHER INFORMATION: Description of Artificial Sequence:5' RACE
      oligonucleotide primer ASEQ2

<400> SEQUENCE: 15
atcgcggaac gca                                                            13

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence:5' RACE
      oligonucleotide primer ASEQ3

<400> SEQUENCE: 16
aaggatccaa gtctacatac ac                                                  22

<210> SEQ ID NO 17
<211> LENGTH: 5
<212> TYPE: PRT
<213> ORGANISM: Artificial Sequence
<220> FEATURE:
<223> OTHER INFORMATION: Description of Artificial Sequence:peptide
      fragment #47 from in-gel trypsin digestion
<221> NAME/KEY: MOD_RES
<222> LOCATION: (2)
<223> OTHER INFORMATION: Xaa = unsure amino acid

<400> SEQUENCE: 17

Val Xaa Val Pro Arg
 1               5

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence:peptide
      fragment #62 from in-gel trypsin digestion
<221> NAME/KEY: MOD_RES
<222> LOCATION: (1)
<223> OTHER INFORMATION: Xaa = unsure amino acid

<400> SEQUENCE: 18

Xaa Pro Ser Asn Glu Ile Phe Ser Arg
 1               5

<210> SEQ ID NO 19
<211> LENGTH: 8
<212> TYPE: PRT
<213> ORGANISM: Artificial Sequence
<220> FEATURE:
<223> OTHER INFORMATION: Description of Artificial Sequence:peptide
      fragment #88 from in-gel trypsin digestion
<221> NAME/KEY: MOD_RES
<222> LOCATION: (1)..(2)
<223> OTHER INFORMATION: Xaa = unsure amino acid

<400> SEQUENCE: 19

Xaa Xaa Pro Asn Val Val Pro Lys
 1               5

<210> SEQ ID NO 20
<211> LENGTH: 10
<212> TYPE: PRT
<213> ORGANISM: Artificial Sequence
<220> FEATURE:
<223> OTHER INFORMATION: Description of Artificial Sequence:N-terminal
      sequence from Puri-#1
```

```
<400> SEQUENCE: 20

Gly Gly Phe Gly Gly Leu Gly Gly Arg Gly
 1               5                   10

<210> SEQ ID NO 21
<211> LENGTH: 10
<212> TYPE: PRT
<213> ORGANISM: Artificial Sequence
<220> FEATURE:
<223> OTHER INFORMATION: Description of Artificial Sequence:N-terminal
      sequence from Puri-#2

<400> SEQUENCE: 21

Gly Phe Gly Gly Phe Gly Gly Leu Gly Gly
 1               5                   10

<210> SEQ ID NO 22
<211> LENGTH: 10
<212> TYPE: PRT
<213> ORGANISM: Artificial Sequence
<220> FEATURE:
<223> OTHER INFORMATION: Description of Artificial Sequence:N-terminal
      sequence from Puri-#3

<400> SEQUENCE: 22

Phe Gly Gly Phe Gly Gly Phe Gly Gly Leu
 1               5                   10
```

BEE VENOM PROTEIN AND GENE ENCODING SAME

CROSS REFERENCES TO RELATED APPLICATIONS

This application claims the benefit of U.S. Provisional Application No. 60/100,172, filed Sep. 14, 1998, which is incorporated herein by reference in its entirety for all purposes.

FIELD OF THE INVENTION

This invention relates to the field of cloning and expression of a protein with therapeutic value in the treatment of various diseases, especially inflammatory diseases such as rheumatoid arthritis. More specifically, the invention relates to a novel protein called PX3.101 purified from honey bee venom and the gene encoding the protein.

BACKGROUND OF THE INVENTION

The immune system plays a critical beneficial role in combating infections. However, in some instances improper immune responses can result in many disabling diseases. Autoimmune or immune-system mediated diseases may be either B-cell mediated (i.e., antibody-mediated) or T-cell mediated. Many autoimmune diseases involve an undesirable inflammatory response. Examples of such diseases include rheumatoid arthritis, chronic hepatitis, Crohn's disease, psoriasis, vasculitis, and the like.

Existing therapies for autoimmune diseases, particularly those involving an undesirable inflammatory response are inadequate. Most immune system-mediated diseases are chronic conditions that require the prolonged administration of drugs to address the symptoms of the disease. Accordingly, an important criterion for drugs used to treat these diseases is low toxicity. However, many drugs utilized to treat autoimmune diseases (e.g., steroids and non-steroidal anti-inflammatory compounds (NSAIDs)), have significant toxic side effects that become manifest after prolonged periods of use. Various immunosuppressive drugs (e.g., cyclosporin A and azathioprine) have also been used to treat autoimmune diseases. However, these compounds are relatively non-specific and have the adverse effect of weakening the entire immune system, thus leaving the patient susceptible to infectious disease.

A variety of inflammatory diseases, including rheumatoid arthritis, are associated with interleukin 8 (IL-8). IL-8 is a chemokine that promotes the recruitment and activation of neutrophil leukocytes and represents one of several endogenous mediators of acute inflammatory response. IL-8 has also been variously referred to as neutrophil-activating factor, monocyte-derived neutrophil chemotactic factor, interleukin-8 (IL-8) and neutrophil-activating peptide. The term IL-8 has gained the most widespread acceptance and is used herein.

Inflammation and autoimmune responses commence with the migration of leukocytes out of the microvascular into the extravascular space in response to chemoattractant molecules. Chemoattractants may originate from the host and include chemokines and activated complement components, or may be released from an invading organism. Once exposed to chemoattractants within the vasculature, the leukocytes become activated and capable of adhering to the endothelium providing the first step in the development of inflammation. Stimulated neutrophils adhere to the endothelium of the microvasculature in response to a gradient of chemoattractants which direct the cells into the extravascular space toward the source of the chemoattractant. See, for example, Anderson et al., *Journal Clin. Invest.* 74:536–551, (1984); Ley, K. et al., *Blood* 77:2553–2555, (1991); Paulson, J. C., "Selectincarbohydrate-mediated adhesion of leukocytes", *Adhesion: Its Role in Inflammatory Disease,* W. H. Freeman, 1992; Lasky, L. A., "The homing receptor" (LECAM 1/L-selectin), *Adhesion: Its role in inflammatory disease,* W. H. Freeman, (1992).

Rheumatoid arthritis is one of the more prevalent autoimmune and inflammatory diseases. The disease afflicts approximately 1% of the total population and about 2.5 million persons in the United States alone. Direct prescription usage is estimated at $5.6 billion worldwide. For individuals suffering from rheumatoid arthritis, the individual's immune system mistakenly perceives the body's own joint tissue as foreign and thus initiates an abnormal immune response. The disease is characterized by chronic inflammation, destruction of cartilage, and ultimately bone erosion and the destruction of joints.

As with other inflammatory diseases, known treatments for IL-8 mediated diseases and rheumatoid arthritis can include the use of nonspecific immunosuppressive drugs that suppress the entire immune system; as noted above, however, such treatments put the patient at risk for contacting an infectious disease. Prolonged use of such drugs can also result in severe side effects. Moreover, immunosuppressive drugs are only partially effective in mitigating the symptoms of rheumatoid arthritis and the utility of the treatment tends to decrease with time.

Other therapies currently used are non-steroid anti-inflammatory drugs (NSAIDs), corticosteroids and a variety of disease modifying anti-rheumatic drugs (DMARDs). There is general dissatisfaction with these drugs for two major reasons: (i) incidence of adverse side effects, which lead to over 700, 000 hospitalizations every year, and (ii) inability to reverse disease progression.

Given the paucity of effective treatments for inflammatory diseases and autoimmune diseases generally, and the need for effective compositions for treating diseases associated with IL-8 such as rheumatoid arthritis more particularly, there is a significant need for new substances that can be used in the treatment of these diseases.

The present invention provides novel isolated proteins and nucleic acids encoding the proteins that are effective in treating autoimmune and inflammatory diseases, especially rheumatoid arthritis. The peptides of the invention also can inhibit the binding of IL-8 to its receptor and inhibit a variety of enzymes associated with inflammatory diseases.

SUMMARY OF THE INVENTION

The invention provides nucleic acid molecules that include a polynucleotide sequence that encodes a PX3.101 polypeptide or fragments thereof. The polypeptides of the invention have an amino acid sequence at least 75% identical to an amino acid sequence as set forth in SEQ ID NO:2 over a region at least about 40 amino acids in length when compared using the BLASTP algorithm with a wordlength (W) of 3, and the BLOSUM62 scoring matrix. The polynucleotide sequences are preferably at least 75% identical to a nucleic acid sequence set forth in residues 74 to 349 of SEQ ID NO:1 over a region of at least 50 nucleotides in length when compared using the BLASTN algorithm with a wordlength (W) of 11, M=5, and N=-4.

Nucleic acids of the invention also include isolated nucleic acid molecules comprising a nucleotide sequence selected from the group consisting of: (a) deoxyribonucleotide sequence complementary to nucleotides 74 to 349 of SEQ ID NO:1; (b) a ribonucleotide sequence complementary to nucleotides 74 to 349 of SEQ ID NO:1; (c) a nucleotide sequence complementary to the deoxyribonucleotide sequence of (a) or to the ribonucleotide sequence of (b); (d) a nucleotide sequence of at least 23 consecutive nucleotides capable of hybridizing to nucleotides 74 to 349 of SEQ ID NO:1; and (e) a nucleotide sequence capable of hybridizing to a nucleotide sequence of (d). The nucleic acid molecules of the invention will generally hybridize to a polynucleotide sequence consisting of nucleotides 74 to 349 of SEQ ID NO:1 under stringent conditions. An exemplary nucleic acid of the invention is a nucleic acid consisting of nucleotides 74 to 349 of SEQ ID NO:1. Nucleic acids of the invention also include those which are capable of being amplified with forward primer 5' AAGGATCCACAGTGCAACGTAAGTTC 3' (SEQ ID NO:3) and reverse primer 5' ACTGATAAAATAATAAC 3' (SEQ ID NO:5).

The invention also provides polypeptides that have an amino acid sequence at least 75% identical to an amino acid sequence as set forth in SEQ ID NO:2 over a region at least 40 amino acids in length when compared using the BLASTP algorithm with a wordlength (W) of 3, and the BLOSUM62 scoring matrix. Polypeptides of the invention include polypeptides encoded by a nucleic acid segment that hybridizes under stringent conditions to a nucleic acid fragment having the sequence set forth in SEQ ID NO:1. Polypeptides that are also included are those having an antigenic determinant common to a polypeptide comprising the amino acid sequence set forth in SEQ ID NO:2. An example of a polypeptide of the invention is a polypeptide having the sequence set forth in SEQ ID NO:2. The invention further provides polypeptide fragments that include at least 12 contiguous amino acids from SEQ ID NO:2. Other polypeptides provided by the invention are purified polypeptides which include a signal peptide, at least 3 GGX repeats, and a C terminal segment extending from the last GGX repeat to the C-terminus which contains at least 7 cysteine residues, wherein X is any amino acid and the polypeptide is less than 140 amino acids in length.

The invention also includes cells that include a vector containing a nucleic acid of the invention. For example, the invention provides cells that have a recombinant expression cassette containing a promoter operably linked to a polynucleotide sequence which encodes a polypeptide as described herein. Both prokaryotic and eukaryotic cells that express polypeptides of the invention are provided.

Methods for producing a polypeptide comprising the amino acid sequence of SEQ ID NO:2 or fragments thereof are also provided. The methods generally include culturing a host cell containing a recombinant expression cassette under conditions suitable for the expression of the polypeptide and then recovering the polypeptide from the host cell culture.

The invention further provides antibodies that are specific for the polypeptides and polypeptide fragments of the invention.

A variety of pharmaceutical compositions are provided by the invention. These compositions typically contain a polypeptide as described herein and a pharmaceutically acceptable excipient. In some instances, the compositions also include a complementary agent which is known to be effective in treating inflammatory diseases. Various compositions can be used to treat various diseases, including, for example, inflammatory diseases, cancer, autoimmune diseases, pain, and diseases associated with chemokine imbalances. These methods generally involve administering a therapeutically effective dose of one of the pharmaceutical compositions of the invention to a patient suffering from a disease.

The invention further provide methods for inhibiting the interaction between certain chemokines with their receptors or for inhibiting enzymes associated with inflammatory diseases. These method generally involve admixing a polypeptide of the invention with a solution containing a chemokine and its receptor or a solution containing an enzyme associated with inflammatory diseases.

BRIEF DESCRIPTION OF THE DRAWINGS

FIG. 2 shows elution profiles for the three HPLC purification steps used to purify PX3.101 protein.

FIG. 3A shows the full-length nucleotide sequence for the cDNA encoding full-length PX3.101 (SEQ ID NO:1) and the predicted protein sequence of PX3.101 (SEQ ID NO:2). The nucleotide sequence is the number listed on the left in plain type; the sequence begins with the first nucleotide of the PX3.101 cDNA. Amino acids are numbered in italics on the right. The in-frame stop codon is denoted by an asterisk. Four peptide sequences obtained from peptide sequencing are underlined.

FIG. 3B is a schematic representation of the PX3.101 protein structure showing the signal peptide region, the region containing Gly Gly Xaa (where Xaa=any amino acid and Gly=Glycine) repeats and the cysteine rich region.

FIG. 5 includes photographs of representative joint tissues from mice in different treatment groups.

DEFINITIONS

Figure 1:
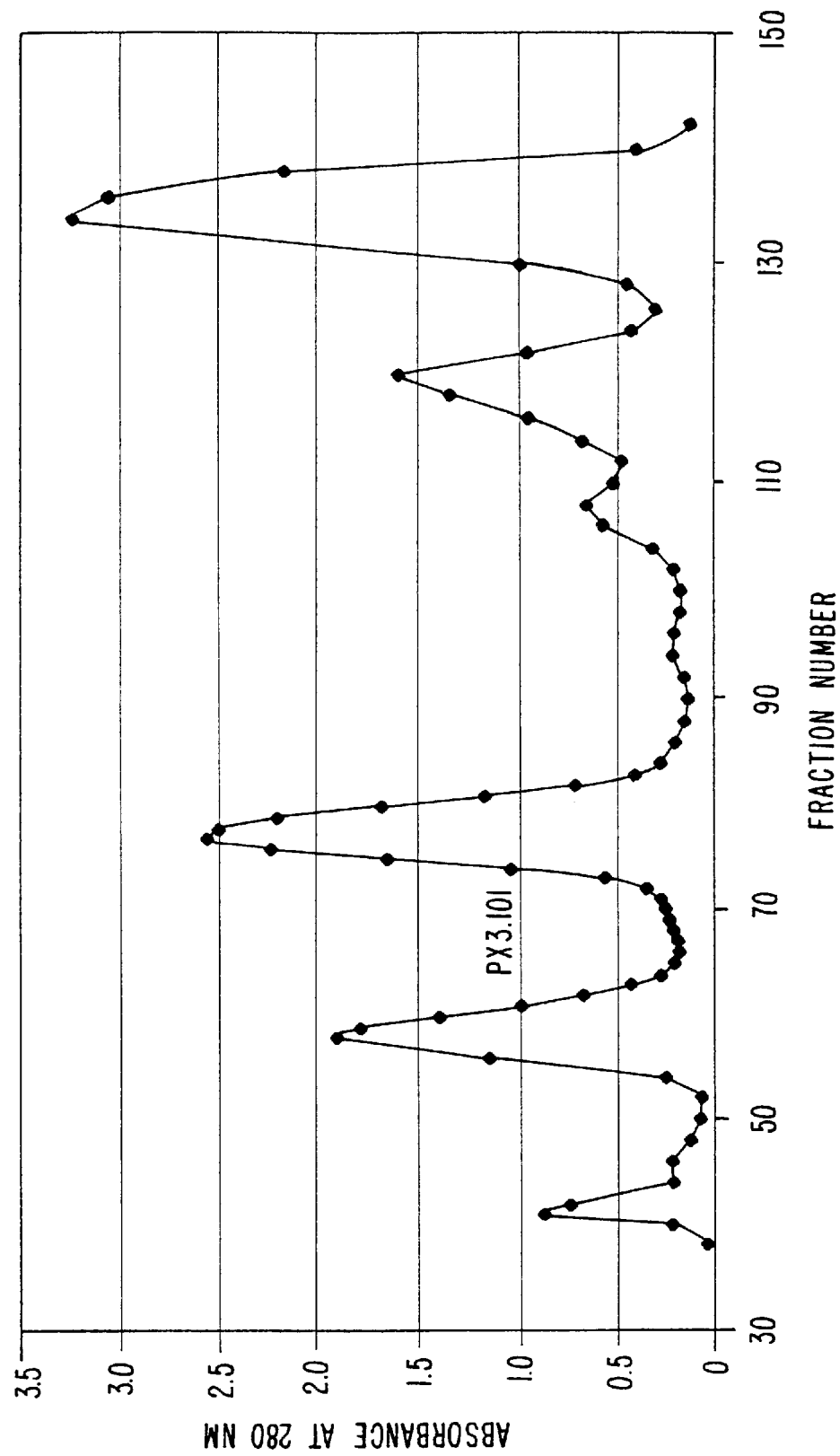
FIG. 1 shows an elution profile for a honey bee venom suspension eluted through a Sephadex G-50 sizing column. One ml of honeybee venom suspension (approximate 0.5 g solid material) was diluted in 10 ml of column buffer (ammonium formate buffer, 0.1 M, pH 4.6), spun down and filtered through a 0.45 $\mu$m filter. The resulting solution was loaded onto a Sephadex G-50 column (two connected columns, each 1.5×170 cm (diameter×height)) pre-equilibrated with the column buffer. The column was eluted at about 0.6 ml/min, and fractions of 100 drops (approximately 4.0 ml) were collected.

The term "nucleic acid" refers to a deoxyribonucleotide or ribonucleotide polymer in either single- or double-stranded form, and unless otherwise limited, encompasses known analogues of natural nucleotides that hybridize to nucleic acids in a manner similar to naturally-occurring nucleotides. Unless otherwise indicated, a particular nucleic acid sequence includes the complementary sequence thereof. A "subsequence" refers to a sequence of nucleotides or amino acids that comprise a part of a longer sequence of nucleotides or amino acids (e.g., a polypeptide), respectively.

A "probe" is an nucleic acid capable of binding to a target nucleic acid of complementary sequence through one or more types of chemical bonds, usually through complementary base pairing, usually through hydrogen bond formation, thus forming a duplex structure. The probe binds or hybridizes to a "probe binding site." A probe may include natural (i.e. A, G, C, or T) or modified bases (7-deazaguanosine, inosine, etc.). A probe can be an oligonucleotide which is a single-stranded DNA. Oligonucleotide probes can be synthesized or produced from naturally occurring polynucleotides. In addition, the bases in a probe can be joined by a linkage other than a phosphodiester bond, so long as it does not interfere with hybridization. Thus, probes may be peptide nucleic acids in which the constituent bases are joined by peptide bonds rather than phosphodiester linkages (see, for example, Nielsen et al., Science 254, 1497–1500 (1991)). Some probes may have leading and/or trailing sequences of noncomplementarity flanking a region of complementarity.

The terms "polypeptide," "peptide" and "protein" are used interchangeably to refer to a polymer of amino acid residues. The term also applies to amino acid polymers in which one or more amino acids are chemical analogues of a corresponding naturally-occurring amino acids.

The term "operably linked" refers to functional linkage between a nucleic acid expression control sequence (such as a promoter, signal sequence, or array of transcription factor binding sites) and a second polynucleotide, wherein the expression control sequence affects transcription and/or translation of the second polynucleotide.

A "heterologous sequence" or a "heterologous nucleic acid," as used herein, is one that originates from a source foreign to the particular host cell, or, if from the same source, is modified from its original form. Thus, a heterologous gene in a prokaryotic host cell includes a gene that, although being endogenous to the particular host cell, has been modified. Modification of the heterologous sequence can occur, e.g., by treating the DNA with a restriction enzyme to generate a DNA fragment that is capable of being operably linked to the promoter. Techniques such as site-directed mutagenesis are also useful for modifying a heterologous nucleic acid.

The term "recombinant" when used with reference to a cell indicates that the cell replicates a heterologous nucleic acid, or expresses a peptide or protein encoded by a heterologous nucleic acid. Recombinant cells can contain genes that are not found within the native (non-recombinant) form of the cell. Recombinant cells can also contain genes found in the native form of the cell wherein the genes are modified and re-introduced into the cell by artificial means. The term also encompasses cells that contain a nucleic acid endogenous to the cell that has been modified without removing the nucleic acid from the cell; such modifications include those obtained by gene replacement, site-specific mutation, and related techniques.

A "recombinant expression cassette" or simply an "expression cassette" is a nucleic acid construct, generated recombinantly or synthetically, that has control elements that are capable of effecting expression of a structural gene that is operably linked to the control elements in hosts compatible with such sequences. Expression cassettes include at least promoters and optionally, transcription termination signals. Typically, the recombinant expression cassette includes at least a nucleic acid to be transcribed (e.g., a nucleic acid encoding a desired polypeptide) and a promoter. Additional factors necessary or helpful in effecting expression can also be used as described herein. For example, an expression cassette can also include nucleotide sequences that encode a signal sequence that directs secretion of an expressed protein from the host cell. Transcription termination signals, enhancers, and other nucleic acid sequences that influence gene expression, can also be included in an expression cassette.

The term "isolated," "purified" or "substantially pure" means an object species (e.g., PX3.101 polypeptide or fragments thereof, or a nucleic acid fragment) is the predominant macromolecular species present (i.e., on a molar basis it is more abundant than any other individual species in the composition), and preferably the object species comprises at least about 50 percent (on a molar basis) of all macromolecular species present. Generally, an isolated, purified or substantially pure composition will comprise more than 80 to 90 percent of all macromolecular species present in a composition. Most preferably, the object species is purified to essential homogeneity (i e., contaminant species cannot be detected in the composition by conventional detection methods) wherein the composition consists essentially of a single macromolecular species.

The term "complementary" means that one nucleic acid is identical to, or hybridizes selectively to, another nucleic acid molecule. Selectivity of hybridization exists when hybridization occurs that is more selective than total lack of specificity. Typically, selective hybridization will occur when there is at least about 55% identity over a stretch of at least 14–25 nucleotides, preferably at least 65%, more preferably at least 75%, and most preferably at least 90%. Preferably, one nucleic acid hybridizes specifically to the other nucleic acid. See M. Kanehisa, *Nucleic Acids Res.* 12:203 (1984).

The terms "identical" or percent "identity," in the context of two or more nucleic acids or polypeptides, refer to two or more sequences or subsequences that are the same or have a specified percentage of nucleotides or amino acid residues that are the same, when compared and aligned for maximum correspondence, as measured using a sequence comparison algorithm such as those described below for example, or by visual inspection.

The phrase "substantially identical," in the context of two nucleic acids or polypeptides, refers to two or more sequences or subsequences that have at least 75%, preferably at least 85%, more preferably at least 90%, 95% or higher nucleotide or amino acid residue identity, when compared and aligned for maximum correspondence, as measured using a sequence comparison algorithm such as those described below for example, or by visual inspection. Preferably, the substantial identity exists over a region of the sequences that is at least about 40–50 residues in length, preferably over a longer region than 50 amino acids, more preferably at least about 90–100 residues, and most preferably the sequences are substantially identical over the full length of the sequences being compared, such as the coding region of a nucleotide for example.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., supra).

Another example of algorithm that is suitable for determining percent sequence identity and sequence similarity is the BLAST algorithm, which is described in Altschul et al., *J. Mol. Biol.* 215:403–410 (1990). Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra.). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. For identifying whether a nucleic acid or polypeptide is within the scope of the invention, the default parameters of the BLAST programs are suitable. The BLASTN program (for nucleotide sequences) uses as defaults a word length (W) of 11, an expectation (E) of 10, M=5, N=−4, and a comparison of both strands. For amino acid sequences, the BLASTP program uses as defaults a word length (W) of 3, an expectation (E) of 10, and the BLOSUM62 scoring matrix. The TBLATN program (using protein sequence for nucleotide sequence) uses as defaults a word length (W) of 3, an expectation (E) of 10, and a BLOSUM 62 scoring matrix. (see Henikoff & Henikoff, *Proc. Natl. Acad. Sci. USA* 89:10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873–5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

Another indication that two nucleic acid sequences are substantially identical is that the two molecules hybridize to each other under stringent conditions. "Bind(s) substantially" refers to complementary hybridization between a probe nucleic acid and a target nucleic acid and embraces minor mismatches that can be accommodated by reducing the stringency of the hybridization media to achieve the desired detection of the target polynucleotide sequence. The phrase "hybridizing specifically to", refers to the binding, duplexing, or hybridizing of a molecule only to a particular nucleotide sequence under stringent conditions when that sequence is present in a complex mixture (e.g., total cellular) DNA or RNA.

The term "stringent conditions" refers to conditions under which a probe will hybridize to its target subsequence, but to no other sequences. Stringent conditions are sequence-dependent and will be different in different circumstances. Longer sequences hybridize specifically at higher temperatures. Generally, stringent conditions are selected to be about 5° C. lower than the thermal melting point (Tm) for the specific sequence at a defined ionic strength and pH. The Tm is the temperature (under defined ionic strength, pH, and nucleic acid concentration) at which 50% of the probes complementary to the target sequence hybridize to the target sequence at equilibrium. (As the target sequences are generally present in excess, at Tm, 50% of the probes are occupied at equilibrium). Typically, stringent conditions will be those in which the salt concentration is less than about 1.0 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions can also be achieved with the addition of destabilizing agents such as formamide.

A further indication that two nucleic acid sequences or polypeptides are substantially identical is that the polypeptide encoded by the first nucleic acid is immunologically cross reactive with the polypeptide encoded by the second nucleic acid, as described below. The phrases "specifically binds to a protein" or "specifically immunoreactive with," when referring to an antibody refers to a binding reaction which is determinative of the presence of the protein in the presence of a heterogeneous population of proteins and other biologics. Thus, under designated immunoassay conditions, a specified antibody binds preferentially to a particular protein and does not bind in a significant amount to other proteins present in the sample. Specific binding to a protein under such conditions requires an antibody that is selected for its specificity for a particular protein. A variety of immunoassay formats may be used to select antibodies specifically immunoreactive with a particular protein. For example, solid-phase ELISA immunoassays are routinely used to select monoclonal antibodies specifically immunoreactive with a protein. See, e.g., Harlow and Lane (1988) *Antibodies, A Laboratory Manual,* Cold Spring Harbor Publications, New York, for a description of immunoassay formats and conditions that can be used to determine specific immunoreactivity.

"Conservatively modified variations" of a particular polynucleotide sequence refers to those polynucleotides that encode identical or essentially identical amino acid sequences, or where the polynucleotide does not encode an amino acid sequence, to essentially identical sequences. Because of the degeneracy of the genetic code, a large number of functionally identical nucleic acids encode any given polypeptide. For instance, the codons CGU, CGC, CGA, CGG, AGA, and AGG all encode the amino acid arginine. Thus, at every position where an arginine is specified by a codon, the codon can be altered to any of the corresponding codons described without altering the encoded polypeptide. Such nucleic acid variations are "silent variations," which are one species of "conservatively modified variations." Every polynucleotide sequence described herein which encodes a polypeptide also describes every possible silent variation, except where otherwise noted. One of skill will recognize that each codon in a nucleic acid (except AUG, which is ordinarily the only codon for methionine) can be modified to yield a functionally identical molecule by standard techniques. Accordingly, each "silent variation" of a nucleic acid which encodes a polypeptide is implicit in each described sequence.

A polypeptide is typically substantially identical to a second polypeptide, for example, where the two peptides differ only by conservative substitutions. A "conservative substitution," when describing a protein, refers to a change in the amino acid composition of the protein that does not substantially alter the protein's activity. Thus, "conservatively modified variations" of a particular amino acid sequence refers to amino acid substitutions of those amino acids that are not critical for protein activity or substitution of amino acids with other amino acids having similar properties (e.g., acidic, basic, positively or negatively charged, polar or non-polar, etc.) such that the substitutions of even critical amino acids do not substantially alter activity. Conservative substitution tables providing functionally similar amino acids are well-known in the art. See, e.g., Creighton (1984) *Proteins,* W.H. Freeman and Company. In addition, individual substitutions, deletions or additions which alter, add or delete a single amino acid or a small percentage of amino acids in an encoded sequence are also "conservatively modified variations."

The term "naturally-occurring" as applied to an object refers to the fact that an object can be found in nature. For example, a polypeptide or polynucleotide sequence that is present in an organism that can be isolated from a source in nature and which has not been intentionally modified by humans in the laboratory is naturally-occurring.

The term "antibody" refers to a protein consisting of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical immunoglobulin (antibody) structural unit comprises a tetramer. Each tetramer is composed of two identical pairs of polypeptide chains, each pair having one "light" (about 25 kD) and one "heavy" chain (about 50–70 kD). The N-terminus of each chain defines a variable region of about 100 to 110 or more amino acids primarily responsible for antigen recognition. The terms variable light chain (VL) and variable heavy chain (VH) refer to these light and heavy chains respectively.

Antibodies exist as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to VH-CH1 by a disulfide bond. The F(ab)'$_2$ may be reduced under mild conditions to break the disulfide linkage in the hinge region thereby converting the (Fab')$_2$ dimer into an Fab' monomer. The Fab' monomer is essentially an Fab with part of the hinge region (see, *Fundamental Immunology,* W. E. Paul, ed., Raven Press, N.Y. (1993), for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein also includes antibody fragments either produced by the modification of whole antibodies or synthesized de novo using recombinant DNA methodologies. Preferred antibodies include single chain antibodies, more preferably single chain Fv (scFv) antibodies in which a variable heavy and a variable light chain are joined together (directly or through a peptide linker) to form a continuous polypeptide.

A single chain Fv ("scFv" or "scFv") polypeptide is a covalently linked VH::VL heterodimer which may be expressed from a nucleic acid including VH- and VL-encoding sequences either joined directly or joined by a peptide-encoding linker. Huston, et al. *Proc. Nat. Acad. Sci. USA,* 85:5879–5883 (1988). A number of structures for converting the naturally aggregated—but chemically separated light and heavy polypeptide chains from an antibody V region into an scFv molecule which will fold into a three dimensional structure substantially similar to the structure of an antigen-binding site. See, e.g. U.S. Pat. Nos. 5,091,513 and 5,132,405 and 4,956,778.

An "antigen-binding site" or "binding portion" refers to the part of an immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains are referred to as "hypervariable regions" which are interposed between more conserved flanking stretches known as "framework regions" or "FRs". Thus, the term "FR" refers to amino acid sequences that are naturally found between and adjacent to hypervariable regions in immunoglobulins. In an antibody molecule, the three hypervariable regions of a light chain and the three hypervariable regions of a heavy chain are disposed relative to each other in three dimensional space to form an antigen binding "surface". This surface mediates recognition and binding of the target antigen. The three hypervariable regions of each of the heavy and light chains are referred to as "complementarity determining regions" or "CDRs" and are characterized, for example by Kabat et al. *Sequences of proteins of immunological interest,* 4th ed. U.S. Dept. Health and Human Services, Public Health Services, Bethesda, Md. (1987).

The term "antigenic determinant" refers to the particular chemical group of a molecule that confers antigenic specificity.

The term "epitope" generally refers to that portion of an antigen that interacts with an antibody. More specifically, the term epitope includes any protein determinant capable of specific binding to an immunoglobulin or T-cell receptor. Specific binding exists when the dissociation constant for antibody binding to an antigen is $\leq 1$ $\mu$M, preferably $\leq 100$ nM and most preferably $\leq 1$ nM. Epitopic determinants usually consist of chemically active surface groupings of molecules such as amino acids and typically have specific three dimensional structural characteristics, as well as specific charge characteristics.

The term "patient" includes human and veterinary subjects.

DETAILED DESCRIPTION

This invention provides a novel purified protein that the present inventors call PX3.101 which is effective in treating a variety of diseases, especially inflammatory diseases such as rheumatoid arthritis. Also provided are nucleic acids which encode PX3.101, as well as expression cassettes, expression vectors and cells containing same for use in producing PX3.101 poly-peptide and fragments thereof via recombinant methods. The present invention further provides antibodies which specifically bind to the proteins. Pharmaceutical compositions containing the proteins of the invention and methods for treating various diseases using such pharmaceutical compositions are also provided. The invention further provides methods for inhibiting the binding between chemokines and their receptors and methods for inhibiting certain enzymes associated with various inflammatory diseases.

In addition to being useful in treating various diseases such as inflammatory diseases, the protein provided by the present invention is useful in studying interactions between chemokines and receptors therefor and for kinetic and inhibition studies involving enzymes such as cyclooxygenases, phospholipases, and proteases that have been implicated in various inflammatory diseases. The nucleotide and peptide sequences provided by the present invention is also useful to generate primers and/or probes to screen for PX3.101 homologues in different species, particularly in human.

I. Proteins

Figure 3C:
FIG. 3C is a schematic representation of the structures of PX3.101 protein and its potential homologues. The number of the amino acids and accession numbers are included.
Figure 3C:
Figure 3C:

In one embodiment, the present invention provides a substantially pure PX3.101 polypeptide isolated from natural sources, and/or prepared according to recombinant methods, and/or prepared by chemical synthesis, and/or using a combination of recombinant methods and chemical synthesis. PX3.101 polypeptide is exemplified by the amino acid sequence shown in FIG. 3A and SEQ ID NO:2. If isolated from natural sources, PX3.101 is preferably isolated from an insect, particularly from honey bee venom. Full-length PX3.101 has a molecular weight of approximately 7,700 daltons and has a structure characterized by five Gly-Gly-Xaa repeats (Gly=Glycine and Xaa=any amino acid; sometimes simply referred to as GGX) at the amino-terminus and a cysteine-rich motif at the carboxy terminus. As used herein the term "PX3.101" includes the full-length molecule as set forth in SEQ ID NO:2 and other polypeptides having a similar activity. The term also includes the protein lacking the signal sequence (residues 1–19 of SEQ ID NO:2). Also included, for example, are polypeptides having amino acid sequences consisting of residues 22–92 of SEQ ID NO:2, residues 24–92 of SEQ ID NO:2 and residues 26–92 of SEQ ID NO:2.

The invention also includes an isolated polypeptide having an amino acid sequence at least about 75% identical to an amino acid sequence as set forth in SEQ ID NO:2. More preferably, the polypeptide of the invention is at least 80–85% identical, still more preferably at least 90% or 95% identical to the amino acid sequence of SEQ ID NO:2. The region of similarity between PX3.101 and a polypeptide of interest typically extends over a region of at least 40 amino acids in length, more preferably over a longer region than 40 amino acids such as 50, 60, 70 or 80 amino acids, and most preferably over the full length of the polypeptide. One example of an algorithm that is useful for comparing a polypeptide to the amino acid sequence of PX3.101 is the BLASTP algorithm; suitable parameters include a word length (W) of 3, and a BLOSUM62 scoring matrix.

Besides substantially full-length polypeptides, the present invention provides for biologically active fragments of the polypeptides. Biological activity may include effectiveness of the polypeptide in alleviating the symptoms of various inflammatory diseases (for example, rheumatoid arthritis), and/or inhibiting the binding of chemokines (e.g., IL8) with receptors therefor, and/or inhibiting enzymes associated with inflammatory diseases (such proteins include, by way of illustration and not limitation, cyclooxygenases, phospholipases, lipooxygenases, and proteases such as trypsin and cathepsin G). Other examples of significant biological activity include antibody binding (e.g., the fragment competes with a full-length PX3.101 as set forth in SEQ ID NO:2) and immunogenicity (i.e., possession of epitopes that stimulate B- or T-cell responses against the fragment).

The invention further provides a subsequence which ordinarily comprises at least 5 contiguous amino acids, typically at least 6 or 7 contiguous amino acids, more typically 8 or 9 contiguous amino acids, usually at least 10, 11 or 12 contiguous amino acids, preferably at least 13 or 14 contiguous amino acids, more preferably at least 16 contiguous amino acids, and most preferably at least 20, 40, 60 or 80 contiguous amino acids. Other examples of subsequences provided by the invention are amino acid sequences wherein 1 to 10 amino acids are removed from the N-terminal end of PX3.101 (i.e., residues 1–10 of SEQ ID NO:2). Examples of such polypeptides are listed in Table II below, wherein 2, 4 or 6 amino acids are missing from the N-terminal end of full-length PX3.101.

Polypeptides of the invention also include particular regions or domains of the amino acid sequence as set forth in SEQ ID NO:2. For example, polypeptides of the invention include the signal region (from residue 1 to 19 of SEQ ID NO:2), a region containing GGX repeats (from residue 20 to 34 of SEQ ID NO:2; also referred to as the GGX protein or peptide) and a cysteine rich region at the C-terminus (from residue 35 to 92 of SEQ ID NO:2) which is characterized by a specific cysteine pattern CXCXXG (C=Cysteine, G=Glycine, and X=any amino acid).

The polypeptides of the invention are typically encoded by nucleotide sequences that are substantially identical with the nucleotide sequence set forth in SEQ ID NO:1 and shown in FIG. 3A. The nucleotides encoding the polypeptides of the invention will also typically hybridize to the polynucleotide sequence set forth in SEQ ID NO:1.

Often the polypeptides of the invention will share at least one antigenic determinant in common with the amino acid sequence set forth in SEQ ID NO:2. The existence of such a common determinant is evidenced by cross-reactivity of the variant protein with any antibody prepared against PX3.101 polypeptide. Cross-reactivity may be tested using polyclonal sera against PX3.101, but can also be tested using one or more monoclonal antibodies against PX3.101.

The invention further includes the polypeptides described herein in which the polypeptide includes modified polypeptide backbones. Illustrative examples of such modifications include chemical derivatizations of polypeptides, such as acetylations and carboxylations. Modifications also include glycosylation modifications and processing variants of a typical polypeptide. Such processing steps specifically include enzymatic modifications, such as ubiquitinization and phosphorylation. See, e.g., Hershko & Ciechanover, Ann. Rev. Biochem. 51:335–364 (1982).

The polypeptides provided by the invention also include isolated polypeptides comprising a signal peptide, a segment containing multiple GGX repeats (where G is glycine and N is any amino acid), and a C-terminal segment extending from the last GGX repeat to the C-terminus which contains multiple cysteine residues. As used herein, a signal peptide or sequence is a sequence which is capable of mediating the transport of a polypeptide to the cell surface or exterior of intracellular membranes. The polypeptide is typically at least 50, 60, 70, 80 or 90 amino acids long, or any of the lengths therebetween. The polypeptide generally is no longer than 150, 140, 130, 120, 110 or 100 amino acids, or any length therebetween. The segment containing multiple GGX repeats typically contains at least 3 or 4 repeats, and in other instances contains 5 repeats, although more repeats are possible. The number of cysteines in the C-terminal segment is typically at least 5, but may be 6, 7, 8, 9, 10, 11 or 12. More cysteines than this may also be included within this segment. In one particular polypeptide, the polypeptide includes a signal sequence, a segment containing 5 GGX repeats and a C-terminal segment which includes 10 cysteines.

II. Nucleic Acids

The present invention further provides isolated and/or recombinant nucleic acids that encode the entire PX3.101 protein (SEQ ID NO:2) or subsequences thereof which have PX3.101 activity. The nucleic acids of the invention can include naturally occurring, synthetic, and intentionally manipulated polynucleotide sequences (e.g., site directed mutagenesis or use of alternate promoters for RNA transcription). The polynucleotide sequence for PX3.101 includes antisense sequences. The nucleic acids of the invention also include sequences that are degenerate as a result of the degeneracy of the genetic code.

The polynucleotide encoding PX3.101 includes the nucleotide sequence as set forth in SEQ ID NO:1 and nucleic acid sequences complementary to that sequence. Also included in the invention are subsequences of the above-described nucleic acid sequences. Such subsequences include, for example, the coding region of SEQ ID NO:1 (nucleotides 74 to 349), as well as subsequences that are at least 17, 18, 19, 20, 21, 22, 23, 24 or 25 nucleotides in length and which hybridize specifically to a nucleic acid which encodes PX3.101. Thus, the invention also includes an isolated nucleic acid molecule comprising a nucleotide sequence selected from the group consisting of (a) a deoxyribonucleotide sequence complementary to nucleotides 74 to 349 of SEQ ID NO:1; (b) a ribonucleotide sequence complementary to nucleotides 74 to 349 of SEQ ID NO:1; (c) a nucleotide sequence complementary to the deoxyribonucleotide sequence of (a) or to the ribonucleotide sequence of (b); (d) a nucleotide sequence of at least 23 consecutive nucleotides capable of hybridizing to nucleotides 74 to 349 of SEQ ID NO:1; and (e) a nucleotide sequence capable of hybridizing to a nucleotide sequence of (d).

The invention further provides nucleic acid molecules that include a polynucleotide sequence that encodes a polypeptide having an amino acid sequence that is substantially identical to the amino acid sequence set forth in SEQ ID NO:2. For example, the invention includes a polynucleotide sequence that encodes a polypeptide having an amino sequence that is at least 75% identical to the amino acid sequence as set forth in SEQ ID NO:2 over a region of at least 40 amino acids in length. More preferably, the polypeptide encoded by the nucleic acid of the invention are at least 80 to 85% identical to the amino acid sequence of SEQ ID NO:2, and still more preferably at least 90% or 95% identical to the amino acid sequence of SEQ ID NO:2 over a region of at least 40 amino acids. In some instances, the region of percent identity extends over a region of 50, 60, 70 or 80 amino acids, and more preferably over the full length of the amino acid sequence set forth in SEQ ID NO:2.

Sequence comparisons of the protein encoded by the nucleic acids of the invention can be performed visually or with a comparison algorithm. One such algorithm is the BLASTP algorithm using a wordlength (W) of 3 and the BLOSUM62 scoring matrix.

The polynucleotide sequences are typically substantially identical to a polynucleotide sequence such as residues 74 to 349 of SEQ ID NO:1. For example, the invention includes polynucleotide sequences that are at least about 75% identical to the nucleic acid SEQ ID NO:1 over a region of at least about 50 nucleotides in length. More preferably, the nucleic acids of the invention are at least 80–85% identical to the nucleic acid sequence shown in SEQ ID NO:1, and still more preferably at least 90–95% identical to the nucleic acid sequence of SEQ ID NO:1 over a region of at least 50 amino acids. In some instances, the region of percent identity extends over a longer region than 50 nucleotides, such as 75, 100, 125, 150, 175, 200, 225 or 250 nucleotides, or over the full length of the encoding region (residues 74 to 349 of SEQ ID NO:1).

To identify nucleic acids of the invention, one can employ a nucleotide sequence comparison algorithm such as are known to those of skill in the art. For example, one can use the BLASTN algorithm. Suitable parameters for use in BLASTN are wordlength (W) of 11, M=5 and N=−4. One example of a nucleic acid of the invention includes a polynucleotide sequence as set forth in SEQ ID NO:1, especially as obtained from an insect such as a bee.

Alternatively, one can identify a nucleic acid of the invention by hybridizing, under stringent conditions, the nucleic acid of interest to a nucleic acid that includes a polynucleotide sequence of SEQ ID NO:1. The invention also includes nucleic acids which encode a polypeptide which is immunologically cross reactive with PX3.101 or subsequences thereof.

Nucleic acid sequences of the present invention can be obtained by any suitable method known in the art, including, for example, 1) hybridization of genomic or cDNA libraries with probes to detect homologous nucleotide sequences; 2) antibody screening of expression libraries to detect cloned DNA fragments with shared structural features; 3) various amplification procedures such as polymerase chain reaction (PCR) using primers capable of annealing to the nucleic acid of interest; 4) direct chemical synthesis.

In one embodiment, a nucleic acid of the invention is isolated by routine cloning methods. The nucleotide sequence of a gene or cDNA encoding PX3.101 as provided herein, is used to provide probes that specifically hybridize to a PX3.101 cDNA in a cDNA library, a PX3.101 gene in a genomic DNA sample, or to a PX3.101 mRNA in a total RNA sample (e.g., in a Southern or Northern blot). Once the target nucleic acid is identified, it can be isolated according to standard methods known to those of skill in the art.

The desired nucleic acids can also be cloned using well-known amplification techniques. Examples of protocols sufficient to direct persons of skill through in vitro amplification methods, including the polymerase chain reaction (PCR) the ligase chain reaction (LCR), Qβ-replicase amplification and other RNA polymerase mediated techniques, are found in Berger, Sambrook, and Ausubel, as well as Mullis et al. (1987) U.S. Pat. No. 4,683,202; *PCR Protocols A Guide to Methods and Applications* (Innis et al. eds) Academic Press Inc. San Diego, Calif. (1990) (Innis); Arnheim & Levinson (Oct. 1, 1990) *C&EN* 36–47; *The Journal Of NIH Research* (1991) 3: 81–94; (Kwoh et al (1989) *Proc. Natl. Acad. Sci. USA* 86: 1173; Guatelli et al. (1990) *Proc. Natl. Acad. Sci. USA* 87: 1874; Lomell et al. (1989) *J. Clin. Chem.* 35: 1826; Landegren et al. (1988) *Science* 241: 1077–1080; Van Brunt (1990) *Biotechnology* 8: 291–294; Wu and Wallace (1989) *Gene* 4: 560; and Barringer et al. (1990) *Gene* 89: 117. Improved methods of cloning in vitro amplified nucleic acids are described in Wallace et al., U.S. Pat. No. 5,426,039. Suitable primers for use in the amplification of the nucleic acids of the invention include, for example, forward primer ASEQ10: 5' AAGGATCCA-CAGTGCAACGTAAGTTC 3' (SEQ ID NO:3), forward primer ASEQ11: 5' AAGGATCCGGAGGATTTGGAG-GATTTGGAGGATTTGGAGGACTTGGAGGACGTGG 3' (SEQ ID NO:4), reverse primer ASEQ13: 5'ACT-GATAAAATAATAAC 3' (SEQ ID NO:5), reverse primer ASEQ14: 5' ATGAATGATAAAATAC 3' (SEQ ID NO:6), reverse primer ASEQ15: 5'TTATAAAAGTCATCCGC 3'(SEQ ID NO:7).

As an alternative to cloning a nucleic acid, a suitable nucleic acid can be chemically synthesized. Direct chemical synthesis methods include, for example, the phosphotriester method of Narang et al. (1979) *Meth. Enzymol.* 68: 90–99; the phosphodiester method of Brown et al. (1979) *Meth. Enzymol.* 68: 109–151; the diethylphosphoramidite method of Beaucage et al. (1981) *Tetra. Lett.*, 22: 1859–1862; and the solid support method of U.S. Pat. No. 4,458,066. Chemical synthesis produces a single stranded oligonucleotide. This can be converted into double stranded DNA by hybridization with a complementary sequence, or by polymerization with a DNA polymerase using the single strand as a template. One of skill would recognize that while chemical synthesis of DNA is often limited to sequences of about 100 bases, longer sequences may be obtained by the ligation of shorter sequences. Alternatively, subsequences may be cloned and the appropriate subsequences cleaved using appropriate restriction enzymes. The fragments can then be ligated to produce the desired DNA sequence.

In some embodiments, it may be desirable to modify the nucleic acids of the invention. One of skill will recognize many ways of generating alterations in a given nucleic acid construct. Such well-known methods include site-directed mutagenesis, PCR amplification using degenerate oligonucleotides, exposure of cells containing the nucleic acid to mutagenic agents or radiation, chemical synthesis of a desired oligonucleotide (e.g., in conjunction with ligation and/or cloning to generate large nucleic acids) and other well-known techniques. See, e.g., Giliman and Smith (1979) *Gene* 8:81–97, Roberts et al. (1987) *Nature* 328: 731–734.

III. Methods for Preparing or Isolating Protein

A. Recombinant Technologies

1. General

The nucleotide and amino acid sequences of PX3.101 as shown in SEQ ID NO:1 and SEQ ID NO:2, respectively, and corresponding sequences for other variants as described above, allow for production of full-length PX3.101 polypeptide and fragments thereof. Such polypeptides can be produced in prokaryotic or eukaryotic host cells by expression of polynucleotides encoding PX3.101 or fragments thereof. The cloned DNA sequences are expressed in hosts after the sequences have been operably linked to an expression control sequence in an expression vector. Expression vectors are typically replicable in the host organisms either as episomes or as an integral part of the host chromosomal DNA. Commonly, expression vectors contain selection markers, e.g., tetracycline resistance or hygromycin resistance, to permit detection and/or selection of those cells transformed with the desired DNA sequences (see, e.g., U.S. Pat. No. 4,704,362).

2. Expression Cassettes and Host Cells for Expressing Polypeptides

Typically, the polynucleotide that encodes a polypeptide of the invention is placed under the control of a promoter that is functional in the desired host cell to produce relatively large quantities of a polypeptide of the invention. An extremely wide variety of promoters are well-known, and can be used in the expression vectors of the invention, depending on the particular application. Ordinarily, the promoter selected depends upon the cell in which the promoter is to be active. Other expression control sequences such as ribosome binding sites, transcription termination sites and the like are also optionally included. Constructs that include one or more of these control sequences are termed "expression cassettes." Accordingly, the invention provides expression cassettes into which the nucleic acids that encode the polypeptides described herein are incorporated for high level expression in a desired host cell.

In a preferred embodiment, the expression cassettes are useful for expression of the polypeptides of the invention in prokaryotic host cells. Commonly used prokaryotic control sequences, which are defined herein to include promoters for transcription initiation, optionally with an operator, along with ribosome binding site sequences, include such commonly used promoters as the beta-lactamase (penicillinase) and lactose (lac) promoter systems (Change et al. (1977) *Nature* 198: 1056), the tryptophan (trp) promoter system (Goeddel et al. (1980) *Nucleic Acids Res.* 8: 4057), the tac promoter (DeBoer et al. (1983) *Proc. Natl. Acad. Sci. U.S.A.* 80:21–25); and the lambda-derived $P_L$ promoter and N-gene ribosome binding site (Shimatake et al. (1981) *Nature* 292: 128). The particular promoter system is not critical to the invention, any available promoter that functions in prokaryotes can be used.

For expression of polypeptides in prokaryotic cells other than *E. coli*, a promoter that functions in the particular prokaryotic species is required. Such promoters can be obtained from genes that have been cloned from the species, or heterologous promoters can be used. For example, the hybrid trp-lac promoter functions in Bacillus in addition to *E. coli*.

For expression of the polypeptides in yeast, convenient promoters include GAL1-10 (Johnson and Davies (1984) *Mol. Cell. Biol.* 4:1440–1448) ADH2 (Russell et al. (1983) *J. Biol Chem.* 258:2674–2682), PHO5 (*EMBO J.* (1982) 6:675–680), and MFα (Herskowitz and Oshima (1982) in *The Molecular Biology of the Yeast Saccharomyces* (eds. Strathern, Jones, and Broach) Cold Spring Harbor Lab., Cold Spring Harbor, N.Y., pp. 181–209). Another suitable promoter for use in yeast is the ADH2/GAPDH hybrid promoter as described in Cousens et al., *Gene* 61:265–275 (1987). Other promoters suitable for use in eukaryotic host cells are well-known to those of skill in the art.

For expression of the polypeptides in mammalian cells, convenient promoters include CMV promoter (Miller, et al., *BioTechniques* 7:980), SV40 promoter (de la Luma, et al.,(1998) *Gene* 62:121), RSV promoter (Yates, et al, (1985) *Nature* 313:812), MMTV promoter (Lee, et al,(1981) *Nature* 294:228).

For expression of the polypeptides in insect cells, the convenient promoter is from the baculovirus *Autographa Californica* nuclear polyhedrosis virus (NcMNPV) (Kitts, et al., (1993) *Nucleic Acids Research* 18:5667).

Either constitutive or regulated promoters can be used in the present invention. Regulated promoters can be advantageous because the host cells can be grown to high densities before expression of the polypeptides is induced. High level expression of heterologous proteins slows cell growth in some situations. An inducible promoter is a promoter that directs expression of a gene where the level of expression is alterable by environmental or developmental factors such as, for example, temperature, pH, anaerobic or aerobic conditions, light, transcription factors and chemicals. Such promoters are referred to herein as "inducible" promoters, and allow one to control the timing of expression of the polypeptide. For *E. coli* and other bacterial host cells, inducible promoters are known to those of skill in the art. These include, for example, the lac promoter, the bacteriophage lambda $P_L$ promoter, the hybrid trp-lac promoter (Amann et al. (1983) *Gene* 25: 167; de Boer et al. (1983) *Proc. Nat'l. Acad. Sci. USA* 80: 21), and the bacteriophage T7 promoter (Studier et al. (1986) *J. Mol. Biol.;* Tabor et al. (1985) *Proc. Nat'l. Acad. Sci. USA* 82: 1074–8). These promoters and their use are discussed in Sambrook et al., supra. A particularly preferred inducible promoter for expression in prokaryotes is a dual promoter that includes a tac promoter component linked to a promoter component obtained from a gene or genes that encode enzymes involved in galactose metabolism (e.g., a promoter from a UDP galactose 4-epimerase gene (ga/l)). The dual tac-gal promoter, which is described in PCT Patent Application Publ. No. WO98/20111, provides a level of expression that is greater than that provided by either promoter alone.

Inducible promoters for other organisms are also well-known to those of skill in the art. These include, for example, the arabinose promoter, the lacZ promoter, the metallothionein promoter, and the heat shock promoter, as well as many others.

A ribosome binding site (RBS) is conveniently included in the expression cassettes of the invention that are intended for use in prokaryotic host cells. An RBS in *E. coli,* for example, consists of a nucleotide sequence 3–9 nucleotides in length located 3–11 nucleotides upstream of the initiation codon (Shine and Dalgarno (1975) *Nature* 254: 34; Steitz, *In Biological regulation and development: Gene expression* (ed. R. F. Goldberger), vol. 1, p. 349, 1979, Plenum Publishing, NY).

Selectable markers are often incorporated into the expression vectors used to express the polynucleotides of the invention. These genes can encode a gene product, such as a protein, necessary for the survival or growth of transformed host cells grown in a selective culture medium. Host cells not transformed with the vector containing the selection gene will not survive in the culture medium. Typical selection genes encode proteins that confer resistance to antibiotics or other toxins, such as ampicillin, neomycin, kanamycin, chloramphenicol, or tetracycline. Alternatively, selectable markers may encode proteins that complement auxotrophic deficiencies or supply critical nutrients not available from complex media, e.g., the gene encoding D-alanine racemase for Bacilli. Often, the vector will have one selectable marker that is functional in, e.g., *E. coli,* or other cells in which the vector is replicated prior to being introduced into the host cell. A number of selectable markers are known to those of skill in the art and are described for instance in Sambrook et al., supra. A preferred selectable marker for use in bacterial cells is a kanamycin resistance marker (Vieira and Messing, *Gene* 19: 259 (1982)). Use of kanamycin selection is advantageous over, for example, ampicillin selection because ampicillin is quickly degraded by β-lactamase in culture medium, thus removing selective pressure and allowing the culture to become overgrown with cells that do not contain the vector.

Construction of suitable vectors containing one or more of the above listed components employs standard ligation techniques as described in the references cited above. Isolated plasmids or DNA fragments are cleaved, tailored, and re-ligated in the form desired to generate the plasmids required. To confirm correct sequences in plasmids constructed, the plasmids can be analyzed by standard techniques such as by restriction endonuclease digestion, and/or sequencing according to known methods. A wide variety of cloning and in vitro amplification methods suitable for the construction of recombinant nucleic acids are well-known to persons of skill. Examples of these techniques and instructions sufficient to direct persons of skill through many cloning exercises are found in Berger and Kimmel, *Guide to Molecular Cloning Techniques, Methods in Enzymology,* Volume 152, Academic Press, Inc., San Diego, Calif. (Berger); and Current Protocols in Molecular Biology, F. M. Ausubel et al., eds., *Current Protocols,* a joint venture between Greene Publishing Associates, Inc. and John Wiley & Sons, Inc., (1998 Supplement) (Ausubel).

A variety of common vectors suitable for use as starting materials for constructing the expression vectors of the invention are well-known in the art. For cloning in bacteria, common vectors include pBR322 derived vectors such as pBLUESCRIPT™, pUC18/19, and λ-phage derived vectors. In yeast, vectors which can be used include Yeast Integrating plasmids (e.g., YIp5) and Yeast Replicating plasmids (the YRp series plasmids) pYES series and pGPD-2 for example. Expression in mammalian cells can be achieved, for example, using a variety of commonly available plasmids, including pSV2, pBC12BI, and p91023, pCDNA series, pCMV1, pMAMneo, as well as lytic virus vectors (e.g., vaccinia virus, adeno virus), episomal virus vectors (e.g., bovine papillomavirus), and retroviral vectors (e.g., murine retroviruses). Expression in insect cells can be achieved using a variety of baculovirus vectors, including pFastBac1, pFastBacHT series, pBluesBac4.5, pBluesBacHis series, pMelBac series, and pVL1392/1393, for example.

Translational coupling can be used to enhance expression. The strategy uses a short upstream open reading frame derived from a highly expressed gene native to the translational system, which is placed downstream of the promoter, and a ribosome binding site followed after a few amino acid codons by a termination codon. Just prior to the termination codon is a second ribosome binding site, and following the termination codon is a start codon for the initiation of translation. The system dissolves secondary structure in the RNA, allowing for the efficient initiation of translation. See, Squires et. al. (1988) *J. Biol. Chem.* 263: 16297–16302.

Polypeptides of the invention can be expressed in a variety of host cells, including *E. coli,* other bacterial hosts, yeast, and various higher eukaryotic cells such as the COS, CHO and HeLa cells lines and myeloma cell lines. The host cells can be mammalian cells, plant cells, insect cells or microorganisms, such as, for example, yeast cells, bacterial cells, or fungal cells. Examples of suitable host cells include Azotobacter sp. (e.g., *A. vinelandii*), Pseudomonas sp., Rhizobium sp., Erwinia sp., Escherichia sp. (e.g., *E. coli*), Bacillus, Pseudomonas, Proteus, Salmonella, Serratia, Shigella, Rhizobia, Vitreoscilla, Paracoccus and Klebsiella sp., among many others. The cells can be of any of several genera, including Saccharomyces (e.g., *S. cerevisiae*), Candida (e.g., *C. utilis, C. parapsilosis, C. krusei, C. versatilis, C. lipolytica, C. zeylanoides, C. guilliermondii, C. albicans,* and *C. humicola*), Pichia (e.g., *P. farinosa* and *P. ohmeri*), Torulopsis (e.g. *T. candida, T. sphaerica, T. xylinus, T. famata,* and *T. versatilis*), Debaryomyces (e.g., *D. subglobosus, D. cantarellii, D. globosus, D. hansenii,* and *D. japonicus*), Zygosaccharomyces (e.g., *Z. rouxii* and *Z. bailii*), Kluyveromyces (e.g., *K. marxianus*), Hansenula (e.g., *H. anomala* and *H. jadinii*), and Brettanomyces (e.g., *B. lambicus* and *B. anomalus*). Examples of useful bacteria include, but are not limited to, Escherichia, Enterobacter, Azotobacter, Erwinia, Klebsielia. The commonly used insect cells to produce recombinant proteins are Sf9 cells (derived from *Spodoptera frugiperda* ovarian cells) and High Five cells (derived from *Trichoplusia ni* egg cell homogenates; commercially available from Invitrogen).

The expression vectors of the invention can be transferred into the chosen host cell by well-known methods such as calcium chloride transformation for *E. coli* and calcium phosphate treatment or electroporation for mammalian cells. Cells transformed by the plasmids can be selected by resistance to antibiotics conferred by genes contained on the plasmids, such as the amp, gpt, neo and hyg genes.

Once expressed, the recombinant polypeptides can be purified according to standard procedures of the art, including ammonium sulfate precipitation, affinity columns, ion exchange and/or size exclusivity chromatography, gel electrophoresis and the like (see, generally, R. Scopes, *Protein Purification,* Springer-Verlag, N.Y. (1982), Deutscher, *Methods in Enzymology Vol* 182: *Guide to Protein Purification.,* Academic Press, Inc. N.Y. (1990)). Substantially pure compositions of at least about 90 to 95% homogeneity are preferred, and 98 to 99% or more homogeneity are most preferred. Once purified, partially or to homogeneity as desired, the polypeptides may then be used (e.g., treatment of inflammatory diseases in pre-clinical or clinical studies).

To facilitate purification of the polypeptides of the invention, the nucleic acids that encode the polypeptides can also include a coding sequence for an epitope or "tag" for which an affinity binding reagent is available. Examples of suitable epitopes include the myc and V-5 reporter genes; expression vectors useful for recombinant production of polypeptides having these epitopes are commercially available (e.g., Invitrogen (Carlsbad Calif.) vectors pCDNA3.1/Myc-His and pcDNA3.1/V5-His are suitable for expression in mammalian cells; Invitrogen (Carlsbad, Calif.) vectors pBlueBacHis and Gibco (Gaithersburg, Md.) vectors pFastBacHT are suitable for expression in insect cells). Additional expression vectors suitable for attaching a tag to the proteins of the invention, and corresponding detection systems are known to those of skill in the art, and several are commercially available (e.g., FLAG" (Kodak, Rochester N.Y). Another example of a suitable tag is a polyhistidine sequence, which is capable of binding to metal chelate affinity ligands. Typically, six adjacent histidines are used, although one can use more or less than six. Suitable metal chelate affinity ligands that can serve as the binding moiety for a polyhistidine tag include nitrilo-tri-acetic acid (NTA) (Hochuli, E. (1990) "Purification of recombinant proteins with metal chelating adsorbents" In Genetic Engineering: Principles and Methods, J. K. Setlow, Ed., Plenum Press, NY; commercially available from Qiagen (Santa Clarita, Calif.)).

Other haptens that are suitable for use as tags are known to those of skill in the art and are described, for example, in the Handbook of Fluorescent Probes and Research Chemicals (6th Ed., Molecular Probes, Inc., Eugene Oreg.). For example, dinitrophenol (DNP), digoxigenin, barbiturates (see, e.g., U.S. Pat. No. 5,414,085), and several types of fluorophores are useful as haptens, as are derivatives of these compounds. Kits are commercially available for linking haptens and other moieties to proteins and other molecules. For example, where the hapten includes a thiol, a heterobifunctional linker such as SMCC can be used to attach the tag to lysine residues present on the capture reagent.

B. Naturally-Occurring Polypeptides

Naturally occurring polypeptides of the invention, including full-length PX3.101 and fragments thereof can be isolated using conventional techniques such as affinity chromatography. For example, polyclonal or monoclonal antibodies are raised against previously-purified PX3.101 or fragments thereof and attached to a suitable affinity column by well-known techniques. See, e.g., Hudson & Hay, *Practical Immunology* (Blackwell Scientific Publications, Oxford, UK, 1980), Chapter 8 (incorporated herein by reference in its entirety for all purposes). Peptide fragments are generated from intact PX3.101 by chemical or enzymatic cleavage methods which are known to those with skill in the art. Example II also sets forth a method for purifying PX3.101.

C. Other Methods

Alternatively, the polypeptides of the invention can be synthesized by chemical methods or produced by in vitro translation systems using a polynucleotide template to direct translation. Methods for chemical synthesis of polypeptides and in vitro translation are well-known in the art, and are described further by Berger & Kimmel, *Methods in Enzymology, Volume 152, Guide to Molecular Cloning Techniques*, Academic Press, Inc., San Diego, Calif., 1987 (incorporated herein by reference in its entirety for all purposes).

IV. Antibodies

In another embodiment of the invention, antibodies that are immunoreactive with PX3.101 polypeptide or fragments thereof are provided. The antibodies may be polyclonal antibodies, distinct monoclonal antibodies or pooled monoclonal antibodies with different epitopic specificities. Monoclonal antibodies are made from antigen-containing fragments of the protein by methods that are well-known in the art (see, e.g., Kohler, et al. Nature, 256:495, (1975); and Harlow & Lane, *Antibodies, A Laboratory Manual* (C.S.H.P., NY, 1988), both of which are incorporated herein by reference in their entirety for all purposes).

A. Production of Antibodies

Antibodies that bind to PX3.101 polypeptide or other polypeptides of the invention can be prepared using intact polypeptide or fragments containing small peptides of interest as the immunizing antigen. For example, it may be desirable to produce antibodies that specifically bind to the N- or C-terminal domains of PX3.101. The polypeptide used to immunize an animal can be from natural sources, derived from translated cDNA, or prepared by chemical synthesis and can be conjugated with a carrier protein, if desired. Commonly used carriers include keyhole limpet hemocyanin (KLH), thyroglobulin, bovine serum albumin (BSA), and tetanus toxoid. The coupled peptide is then used to immunize the animal (e.g., a mouse, a rat, or a rabbit).

Techniques for generation of human monoclonal antibodies have also been described but are generally more onerous than murine techniques and not applicable to all antigens. See, e.g., Larrick et al., U.S. Pat. No. 5,001,065, for review (incorporated by reference for all purposes). An alternative approach is the generation of humanized antibodies by linking the complementarity-determining regions or CDR regions (see, e.g., Kabat et al., "Sequences of Proteins of Immunological Interest," U.S. Dept. of Health and Human Services, (1987); and Chothia et al., *J. Mol. Biol.* 196:901–917 (1987)) of non-human antibodies to human constant regions by recombinant DNA techniques. See Queen et al., *Proc. Natl. Acad. Sci. USA* 86:10029–10033 (1989) and WO 90/07861, (incorporated by reference for all purposes). Alternatively, one may isolate DNA sequences which encode a human monoclonal antibody or a binding fragment thereof by screening a DNA library from human B cells according to the general protocol outlined by Huse et al., *Science* 246:1275–1281 (1989) and then cloning and amplifying the sequences which encode the antibody (or binding fragment) of the desired specificity. The protocol described by Huse is rendered more efficient in combination with phage display technology. See, e.g., Dower et al., WO 91/17271 and McCafferty et al., WO 92/01047 (each of which is incorporated by reference for all purposes). Phage display technology can also be used to mutagenize CDR regions of antibodies previously shown to have affinity for the peptides of the present invention. Antibodies having improved binding affinity are selected.

The antibodies can be further purified, for example, by binding to and elution from a support to which the polypeptide or a peptide to which the antibodies were raised is bound. A variety of other techniques known in the art can also be used to purify polyclonal or monoclonal antibodies (see, e.g., Coligan, et al., Unit 9, *Current Protocols in Immunology*, Wiley Interscience, (1994), incorporated herein by reference in its entirety).

It is also possible to use the anti-idiotype technology to produce monoclonal antibodies which mimic an epitope. For example, an anti-idiotypic monoclonal antibody made to a first monoclonal antibody will have a binding domain in the hypervariable region which is the "image" of the epitope bound by the first monoclonal antibody.

B. Use of Antibodies

The antibodies of the invention are useful, for example, in screening cDNA expression libraries and for identifying clones containing cDNA inserts which encode structurally-related, immunocrossreactive proteins. See, for example, Aruffo & Seed, *Proc. Natl. Acad. Sci. USA* 84:8573–8577 (1977) (incorporated herein by reference in its entirety for all purposes). Antibodies are also useful to identify and/or purify immunocrossreactive proteins that are structurally related to native PX3.101 or to fragments thereof used to generate the antibody.

V. Therapeutic Methods and Compositions

A. General

The present invention further provides pharmaceutical compositions comprised of the polypeptides of the present invention, including full-length PX3.101 and fragments thereof. As explained more fully below in Example V, the pharmaceutical compositions of the invention are useful in treating a variety of diseases in both human and veterinary subjects. Diseases which can be treated with certain pharmaceutical compositions of the inventions include a variety of inflammatory diseases and autoimmune diseases, (e.g., rheumatoid arthritis, multiple sclerosis, psoriasis, systemic lupus erythematosus (SLE), Crohn's disease, scleroderma), metastatic cancers, and diseases associated with imbalances in chemokine (e.g., IL8, IL-10, IL-1, and TNF-$\alpha$) production such as Alzheimer disease. Some compositions can also be used to treat pain, i.e., the composition can be used as an analgesic.

Pharmaceutical compositions of the invention are suitable for use in a variety of drug delivery systems. Suitable formulations for use in the present invention are found in *Remington's Pharmaceutical Sciences*, Mace Publishing Company, Philadelphia, Pa., 17th ed. (1985). For a brief review of methods for drug delivery, see, Langer, *Science* 249:1527–1533 (1990).

B. Composition and Delivery

The pharmaceutical compositions used for prophylactic or therapeutic treatment comprise an active therapeutic agent, for example, a PX3.101 protein or fragments thereof, a PX3.101 receptor or fragments thereof, and antibodies and idiotypic antibodies thereto, and a variety of other components. Various subsequences of full-length PX3.101 can be used. For example, the polypeptide composition used in the animal studies described in Example V included peptides having amino acid sequences consisting of residues 20–92, 22–92, 24–92 and 26–92 of SEQ ID NO:2.

In some instances, the efficacy of treatment may be enhanced by using the pharmaceutical compositions of the present invention with other complementary compounds that are known to be effective in the treatment of various diseases, especially inflammatory diseases. For example, the pharmaceutical compositions of the invention may also include a compound effective in treatment of inflammatory diseases, such as rheumatoid arthritis for example. Such compounds include ENBREL (manufactured by Immunex) and INDOMETHACIN (manufactured by Merck), METHOTREXATE (manufactured by Mylan and Roxane Laboratories, Inc.), CELEBREX (manufactured by Mosanto), VIOXX (manufactured by Merck), or CYCLOSPORINE (manufactured by Novartis). Other compounds that can be used to treat inflammatory diseases and which can be combined with certain compositions of the invention can be found in the Physician's Desk Reference (1998), which is incorporated herein by reference in its entirety. The complementary compounds used in combination with PX3.101, fragments thereof and/or antibodies thereto, typically have a different mode of action than PX3.101 or fragments thereof and/or differ with respect to the time period during which they are therapeutically effective. Thus, for example, a pharmaceutical composition of the invention includes a therapeutically effective amount of PX3.101 (or an active fragment thereof) in combination with ENBREL since early studies indicate that the two compounds appear to have different mechanisms of action and different time periods during which the therapeutic effect is maintained once treatment is stopped.

The compositions may also include, depending on the formulation desired, pharmaceutically-acceptable, non-toxic carriers of diluents, which are defined as vehicles commonly used to formulate pharmaceutical compositions for animal or human administration. The diluent is selected so as not to affect the biological activity of the combination. Examples of such diluents are distilled water, buffered water, physiological saline, PBS, Ringer's solution, dextrose solution, and Hank's solution. In addition, the pharmaceutical composition or formulation may also include other carriers, adjuvants, or non-toxic, nontherapeutic, nonimmunogenic stabilizers, excipients and the like. The compositions may also include additional substances to approximate physiological conditions, such as pH adjusting and buffering agents, toxicity adjusting agents, wetting agents, detergents and the like.

The composition may also include any of a variety of stabilizing agents, such as an antioxidant for example. Moreover, the polypeptides may be complexed with various well-known compounds that enhance the in vivo stability of the polypeptide, or otherwise enhance its pharmacological properties (e.g., increase the half-life of the polypeptide, reduce its toxicity, enhance solubility or uptake). Examples of such modifications or complexing agents include the production of sulfate, gluconate, citrate, phosphate and the like. The polypeptides of the composition may also be complexed with molecules that enhance their in vivo attributes. Such molecules include, for example, carbohydrates, polyamines, amino acids, other peptides, ions (e.g., sodium, potassium, calcium, magnesium, manganese), and lipids.

Further guidance regarding formulations that are suitable for various types of administration can be found in *Remington's Pharmaceutical Sciences,* Mace Publishing Company, Philadelphia, Pa., 17th ed. (1985). For a brief review of methods for drag delivery, see, Langer, *Science* 249:1527–1533 (1990).

The compositions containing the polypeptides can be administered for prophylactic and/or therapeutic treatments. The polypeptide in the pharmaceutical composition typically is present in a therapeutic amount, which is an amount sufficient to remedy a disease state or symptoms, particularly symptoms associated with inflammation, or otherwise prevent, hinder, retard, or reverse the progression of disease or any other undesirable symptoms in any way whatsoever. The concentration of the polypeptide in the pharmaceutical composition can vary widely, i.e., from less than about 0.1% by weight, usually being at least about 1% by weight, to as much as 20% by weight or more.

In therapeutic applications, compositions are administered to a patient already suffering from a disease, as just described, in an amount sufficient to cure or at least partially arrest the symptoms of the disease and its complications. An appropriate dosage of the pharmaceutical composition or polypeptide of the invention is readily determined according to any one of several well-established protocols. For example, animal studies (e.g., mice, rats) are commonly used to determine the maximal tolerable dose of the bioactive agent per kilogram of weight. In general, at least one of the animal species tested is mammalian. The results from the animal studies can be extrapolated to determine doses for use in other species, such as humans for example.

What constitutes an effective dose also depends on the nature and severity of the disease or condition, and on the general state of the patient's health, but will generally range from about 1 to 500 mg of purified protein per kilogram of body weight, with dosages of from about 5 to 100 mg per kilogram being more commonly employed.

In prophylactic applications, compositions containing the compounds of the invention are administered to a patient susceptible to or otherwise at risk of a particular disease or infection. Such an amount is defined to be a "prophylactically effective" amount or dose. In this use, the precise amounts again depends on the patient's state of health and weight. Typically, the dose ranges from about 1 to 500 mg of purified protein per kilogram of body weight, with dosages of from about 5 to 100 mg per kilogram being more commonly utilized.

The pharmaceutical compositions described herein can be administered in a variety of different ways. Examples include administering a composition containing a pharmaceutically acceptable carrier via oral, intranasal, rectal, topical, intraperitoneal, intravenous, intramuscular, subcutaneous, subdermal, transdermal, intrathecal, and intracranial methods.

For oral administration, the active ingredient can be administered in solid dosage forms, such as capsules, tablets, and powders, or in liquid dosage forms, such as elixirs, syrups, and suspensions. The active component(s) can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate. Examples of additional inactive ingredients that may be added to provide desirable color, taste, stability, buffering capacity, dispersion or other known desirable features are red iron oxide, silica gel, sodium lauryl sulfate, titanium dioxide, and edible white ink. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

If desired, it is possible to formulate solid or liquid formulations in an enteric-coated or otherwise protected form. In the case of liquid formulations, the formulation can be mixed or simply coadministered with a protectant, such as a liquid mixture of medium chain triglycerides, or the formulation can be filled into enteric capsules (e.g., of soft or hard gelatin, which are themselves optionally additionally enteric coated). Alternatively, solid formulations comprising the polypeptide can be coated with enteric materials to form tablets. The thickness of enteric coating on tablets or capsules can vary. Typical thickness range from 0.5 to 4 microns in thickness. The enteric coating may comprise'any of the enteric materials conventionally utilized in orally administrable pharmaceutical formulations. Suitable enteric coating materials are known, for example, from *Remington's Pharmaceutical Sciences,* Mace Publishing Company, Philadelphia, 17th ed. (1985); and *Hagars Handbuch der Pharmazeutischen Praxie,* Springer Verlag, 4$^{th}$ ed., Vol. 7a (1971).

Another delivery option involves loading the composition into lipid-associated structures (e.g., liposomes, or other lipidic complexes) which may enhance the pharmaceutical characteristics of the polypeptide component of the composition. The complex containing the composition may subsequently be targeted to specific target cells by the incorporation of appropriate targeting molecules (e.g., specific antibodies or receptors). It is also possible to directly complex the polypeptide with a targeting agent.

Compositions prepared for intravenous administration typically contain 100 to 500 ml of sterile 0.9% NaCl or 5% glucose optionally supplemented with a 20% albumin solution and 100 to 500 mg of a polypeptide of the invention. A typical pharmaceutical composition for intramuscular injection would be made up to contain, for example, 1 ml of sterile buffered water and 1 to 10 mg of the purified polypeptide of the invention. Methods for preparing parenterally administrable compositions are well-known in the art and described in more detail in various sources, including, for example, *Remington's Pharmaceutical Science,* Mack Publishing, Philadelphia, Pa., 17th ed., (1985).

Particularly when the compositions are to be used in vivo, the components used to formulate the pharmaceutical compositions of the present invention are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under GMP conditions.

V. Uses

The pharmaceutical compositions of the present invention can be used to treat a variety of diseases. For example, the pharmaceutical compositions can be used in treating various inflammatory diseases. As described in more detail in Example V, certain compositions of the invention have been shown to be effective in treating rheumatoid arthritis in animal model studies. In particular, PX3.101 inhibits several enzymes that are involved in the pathogenesis of rheumatoid arthritis such as cyclooxygenases, phospholipases, lipoxygenases, and various proteases. PX3.101 polypeptide has also been shown to inhibit interaction between cytokines and their receptors (see Example VI), such as IL-8/CXCR2 interaction for example. IL-8 is a major chemokine that regulates the inflammatory process (see e.g., Harada, et al., (1994) *J. Leukoc. Biol.* 56:559). There is also evidence that links IL-8 to tumor angiogenesis and tumor metastasis (Koch, et al, Science 258:1798). Thus some polypeptides of the invention can be used in treating cancer, autoimmune diseases, and/or other inflammatory diseases associated with chemokine imbalances, especially diseases correlated with IL-8 such as Alzheimer disease.

PX3.101 and other polypeptides of the invention also find use in inhibition and kinetic investigations. For example, PX3.101 can be used in studies into the interaction between chemokines and receptors therefor, for example the interaction between IL-8 and CXCR2 and CXCR1. Methods involving inhibition of chemokines generally involve allowing a quantity of the chemokine and receptor to admix with a polypeptide of the invention. More specifically, the method involves adding a polypeptide of the invention to a sample containing the chemokine and receptor and preferably mixing the resulting mixture. Additions may-be made to an in vitro solution or directly into a patient.

PX3.101 is also useful in studies or treatments involving inhibition of various enzymes such as cyclooxygenases (for example, COX1 and COX2), phospholipases (for example, phospholipase A2 and phospholipase C), lipoxygenase, and various proteases (for example, trypsin and cathepsin G). Such methods generally involve allowing an enzyme, particularly those involved in inflammatory processes, to admix with a polypeptide of the invention. Typically, a quantity of polypeptide is added to a sample containing the enzyme of interest. Here, too, additions may be made into an in vitro solution or directly into a patient.

Based upon the foregoing activities, it is also expected that certain polypeptides of the invention can be useful in treating blood coagulation diseases, accelerating wound healing, UV-light protection, reducing various aging phenomenon and as a pain analgesic.

By using PX3.101 to study the interaction between chemokines and their receptors, or the direct interaction between PX3.101 and a cognate receptor (e.g., the amino acid sequence which binds to a receptor), small molecules which mimic this interaction can be developed, thus enabling the small molecule to be used to obtain a therapeutic effect similar to that obtained using PX3.101.

The nucleotide and peptide sequences of PX3.101 is also useful to generate primers and/or probes to screen for PX3.101 homologues in different species, particularly in human. Human homologues of PX3.101 can be directly used as a therapeutic material or as a target to screen drug candidates for various human diseases.

The following examples are offered to further illustrate specific aspects of the present invention and are not to be interpreted so as to limit the scope of the present invention.

EXAMPLE I

General Methods and Materials

A. Electrophoresis and Western Blotting

SDS polyacrylamide gel electrophoresis (SDS-PAGE) was carried out according to standard methods (Sambrook, et al, *Molecular Cloning: A Laboratory Manual*, $2^{nd}$ ed., Cold Spring Harbor Laboratory Press, 1989). Purified PX3.101 protein was electrophoresed in 10–20% SDS-polyacrylamide gradients gel (BioRad, Richmond, Calif.) and then transferred onto nitrocellulose membrane (Schleicher & Schull, Keene, N.H.). The sera collected from animals treated with PBS or PX3.101 (200 µg/kg) was diluted 1:30 in blocking solution (PBS, 0.2% Tween-20, 5% dry milk). The blot was divided using a mini-protean II multi-screening apparatus and probed with diluted sera. Horseradish Peroxidase (HRP)-conjugated goat anti-mouse IgG at 1:10, 000 dilution was used as the secondary antibodies. Signals were visualized using an ECL (enhanced chemi-luminesence) system.

B. Mass Spectral Analysis

Mass spectral analysis was carried out by Heck Facility at Yale University according to the protocols outlined on their website (http://www.info.med.yale.edu/wmkeck). Matrix assisted laser desorption ionization mass spectrometry (MALDI-MS) was used to determine the molecular weights of the peptide fragments from the trypsin digest of PX3.101, and both MALIDI-MS and electrospray ionization mass spectrometry (ESMS) were used to determine the molecular weights of the purified PX3.101 mutual derivatives. MALDI-MS was carried out on a research grade, VG Tofspec SE instrument equipped with delayed extraction and a reflectron. ESMS was carried out on a Micromass Q-Tof mass spectrometer.

C. Reverse Phase (RP) HPLC

Reverse phase HPLC (RP-HPLC) was performed using a Varian Dynamax Model SD-200 solvent delivery module and a UV detector (Dynamax Absorbance Detector Model UV-C). Data acquisition was achieved by using Varian Dynamax Method (Version 1.4.6) software. A Varian Microsorb-MV C-18 reverse phase column (0.46 cm×25 cm) was typically used for analytical analyses, while a semi-prep C-18 reverse phase column (1.0 cm×25 cm), Varian Dynamax 300 A, was used mainly for purification purposes. Buffers used for elution were Buffer A (water with 0.1% trifluoroacetic acid) and Buffer B (acetonitrile with 0.1% trifluoroacetic acid). Elution was achieved using a discontinuous linear gradient formed from buffers A and B. Columns were run at room temperature. (Flow rate: 1 ml/min for analytical HPLC; 4 ml/min for semi-prep). Peak fractions were collected by hand.

D. HPLC—Ion Exchange Chromatography

HPLC-ion exchange chromatography was also used for the purification of PX3.101. The same solvent delivery system described above was used. A Varian Hydropore strong cation exchange column (0.46 cm×10 cm) was used. Buffers used for elution were Buffer A (0.1 M ammonium formate in water, pH 5.8) and Buffer B (1 M ammonium formate, pH 6.7). Elution was achieved using a discontinuous linear gradient formed from buffers A and B. Columns were run at room temperature at a flow rate of 1 ml/min.

E. Amino Acid Analysis

Amino acid analysis was carried out on a Beckman Model 6300 ion-exchange instrument following a 16 hr hydrolysis at 115° C. in 100 µl of 6 N HCl, 0.2% phenol that also contained 2 nM norleucine. Norleucine served as an internal standard to correct for losses that might occur during sample transfers and drying, etc. After hydrolysis, the HCl was dried in a Speedvac and the resulting amino acids dissolved in 100 µl Beckman sample buffer that contained 2 nM homoserine that acted as a second internal standard to independently monitor transfer of the sample onto the analyzer. The instrument was calibrated with a 2 nM mixture of amino acids and was operated according to the manufacturer's programs and using the manufacturer's buffers. Data analysis was carried out on an external computer using Perkin Elmer/Nelson data acquisition software. Improved quantitation of cysteine was obtained by prior oxidation with performic acid in a second sample. This procedure converted both cysteine and cystine to cysteic acid. Performic acid oxidation may destroy tyrosine.

F. N-terminal Sequencing

Direct N-terminal amino acid sequencing of PX3.101 was carried out as previously described (Stone, et al, In *Techniques in Protein Chemistry*, Academic Press, 1992, New York, 23–34). PX3.101 purified by SDS-PAGE was electroblotted onto a Mini-Problott pure PVDF membrane (Applied Biosystems, Foster City, Calif.). The band was visualized by Ponceau S and cut for N-terminal protein sequencing. Alternatively, PX3.101 from Sephadex G-50 chromatography was farther purified and mutual derivatives were resolved by RP HPLC and HPLC-ion exchange chromatography as described above. N-terminal protein sequencing of either form was carried out by automated Edman degradation with an Applied Biosystems sequencer (Model Procise 494 cLc, Foster City, Calif.). An on-line HPLC-analyzer was used for the identification of phenylthiohydantoin (PTH) amino acids.

G. Internal Sequencing

Internal protein sequencing was performed according to standard methods (Stone, et al. *A Practical Guide to Protein and Peptide Purification for Microsequencing*, $2^{nd}$ ed. Academic Press, 1993, New York, 43–69). A Coumassie Blue stained SDS-PAGE gel band was cut and subjected to in-gel trypsin digestion. Peptide fragments were subsequently extracted and analyzed by LC/MS/MS analysis. The resulted MS/MS spectra were compared with spectra in the National Center for Biotechnology Information (NCBI) non-redundant database to determine whether the protein was known. When no protein was identified using this method, the digest was purified by reverse phase HPLC. Detected peak fractions were collected and selected peptides were subjected to mass spectral analysis. N-terminal amino acid sequencing of these peptides was later carried out as described in Example I.

EXAMPLE II

Protein Purification and Characterization

A. Fractionation of Bee Venom

Lyophilized honeybee venom (approximately 0.5 g) (Apitronic Services, Richmond, British Columbia, Canada) or honeybee venom in suspension (approximate 0.5 g solid material per ml, Sigma, St. Louis, Mis.) was diluted in 10 ml of 0.1M ammonium formate buffer (pH 4.6) to give a solution having a concentration of approximately 0.05 g venom/ml. This solution was centrifuged and filtered through 0.45 µm filter, and then loaded onto a Sephadex G-50 column (two columns, each 1.5×170 cm (diameter× length) that were connected in series) pre-equilibrated with 0.1 M ammonium formate buffer (pH 4.6). The column was eluted at about 0.6 ml/min, and fractions of 100 drops (approximately 4.0 ml) were collected.

Fractions containing PX3.101 (fractions 65 to 72) appeared between the peaks of phospholipase A2 and melittin tetramer (FIG. 1). Fractions in the shoulder peak (fractions 65 to 72) were analyzed by SDS gel electrophoresis. Only one major band was found to have molecular weight lower than phospholipase A2. Protein in this band had an apparent molecular weight of approximately 7700 daltons and was called PX3.101. Melittin monomer has a molecular weight of 3000 daltons.

B. Purification of PX3.101

Figure 2A:
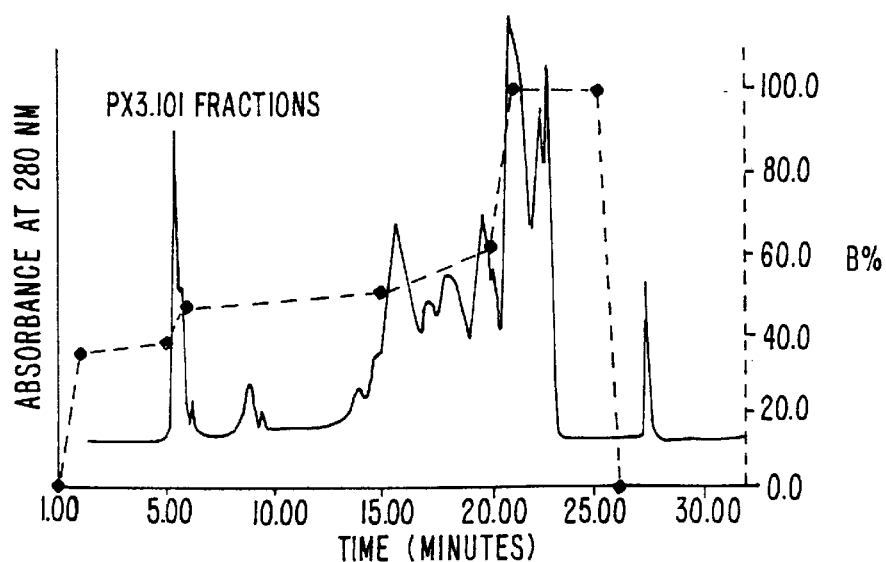
FIG. 2A is an HPLC elution profile for fractions obtained from the G-50 sizing column. Fractions from the G-50 sizing columns such as shown in FIG. 1 were tested for the presence of PX3.101 by SDS-PAGE. Positive fractions were pooled and loaded onto a Reverse Phase (RP) HPLC column (semi-prep C-18 column). The column was eluted with an acetonitrile gradient (see Reverse Phase HPLC section in Example I for detailed information). PX3.101-containing fractions were collected and freeze-dried.
Figure 2B:
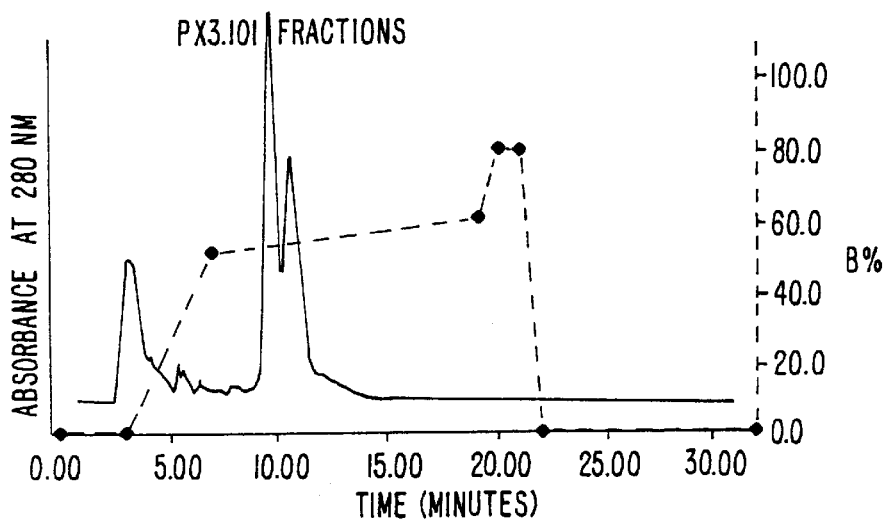
FIG. 2B is an elution profile showing further purification of PX3.101 by ion exchange HPLC in which PX3.101 powder from the first RP-HPLC chromatography purification step was dissolved in 0.1 M ammonium formate (pH 5.8) and loaded onto an ion exchange HPLC column (see Example I for details).

Sephadex G-50 column fractions containing PX3.101 (as identified by SDS PAGE) were pooled and PX3.101 enriched by RP HPLC as described in Example I. A typical elution profile obtained during this RP HPLC step is shown in FIG. 2A. Fractions containing PX3.101 as confirmed by SDS-PAGE and trypsin inhibition assay (data not shown), were freeze-dried and further purified by ion-exchange HPLC as described in Example I. An elution profile is shown in FIG. 2B. A second RP HPLC served as the final step of the purification and was eluted according to the conditions described in Example I. As shown in the elution profile depicted in FIG. 2C, three major peaks were obtained, all of them with shoulders, in this final step. The main peaks were named Puri-#1, Puri-#3 and Puri-#3. These fractions had similar molecular weights based on SDS-PAGE, and all of them showed similar trypsin inhibition activity (data not shown). N-terminal sequencing of the main peaks confirmed that all of them were PX3.101 but with one to several N-terminal amino acids deleted (Table II). These molecules were considered mutual derivatives of PX3.101. These results are consistent with the direct N-terminal sequencing results in which the major PX3.101 band from the SDS-PAGE yielded multiple sequences (see below). The Puri-#1, Puri-#2 and Puri-#3 fractions were combined and used in the animal studies as well as mechanism of action studies of PX3.101 (see Examples V and VI).

C. Characterization

The major gel band from the SDS gel run with G-50 fractions was cut and subjected to in-gel trypsin digestion. The resulting digest was analyzed by LC/MS/MS. Ten to twelve major peptide fragments were formed as a result of digestion and their molecular weights determined (data not shown). No peptides in the NCBI non-redundent database were found to match the predicated molecular weights of peptides from trypsin digestion.

The peptide fragments from the trypsin digestion were then purified by RP-HPLC. Detailed protocols for the purification are described on the website (http://info.med.yale.edu/wmkeck/prochem.htm). The peak fractions (#47, 61, 62, 65, 75, 88 and 106) were collected and further analyzed by mass spectroscopy. Four peptide fragments (fractions #47, 62, 75 and 88) were selected for amino acid sequencing. The amino acid sequences of the peptides are shown in Table I below.

Direct N-terminal sequencing of the major SDS gel band blotted to PVDF membrane was also tried, but yielded multiple amino acids in each cycle of the sequencing (data not shown). This result suggested either major contaminants or the presence of multiple forms of PX3.101 that were mutual derivatives. Further study indicated the presence of multiple forms of this molecule resulted from deletions of different numbers of amino acids from the N-terminus (see below).

Polypeptides contained in collected Fractions from the final RP-HPLC column (i.e., Puri-#1, Puri-#2, and Puri-#3; see FIG. 2C), had similar molecular weights based on SDS-PAGE, and all of them showed similar trypsin inhibition activity (data not shown). N-terminal sequencing of the main peaks confirmed that all of them were PX3.101 but with one to several N-terminal amino acids deleted (Table II). These molecules were considered mutual derivatives of PX3.101. These results are consistent with the direct N-terminal sequencing results in which the major PX3.101 band from the SDS-PAGE yielded multiple sequences (see above).

A predicted molecular weight of about 7,700 daltons correlated well with the migration of PX3.101 on SDS-gel but did not correspond well with where the protein eluted in the elution profile for the Sephadex G-50 sizing column. The fact that the fraction containing PX3.101 eluted between Phospholipase A2 (MW 19,000) and melittin tetramer (11, 400) indicated an apparent molecular weight between 11,400 and 19,000. This discrepancy suggested that either the PX3.101 was present as a dimer, or that there was significant post-translational modification of the protein. Gel electrophoresis results obtained under non-reducing condition indicated the presence of dimers of PX3.101 molecules (data not shown).

A glucose assay did not show any glycosylation of PX3.101 (data not shown). The molecular weights of Puri-#1, Puri-#2 and Puri-#3, as determined by mass spectral analysis matched well with the molecular weights predicted from their amino acid sequences (Table II). These results suggested that there are no post-translational modifications of these derivatives. The C-terminals of these mutual derivatives are likely to be intact and to be the same.

The amino acid analysis of the purified PX3.101 used for animal studies showed that it had an extinction coefficient at 280 nm of 0.286 ml/mg/cm. Protein amount in any given preparation was determined by its absorbance at 280 nm and the extinction coefficient.

EXAMPLE III

Cloning PX3.101 cDNA and Predicted Protein Sequence

A. Method

The degenerate oligonucleotide primer (5' ATGGATC-CAAYGARATHTTYWSNAG 3'—SEQ ID NO:8) Y=C or T; R=A or G; H=A or C or T; W=A or T; N=A or C or G or T) was designed based on the amino acid sequence (NEIFSR—SEQ ID NO:9) obtained from protein sequencing. All the PX3.101 primers and Oligo(dT) (5'TTGCGGCCGCTTTTTTTTTTTTTTTTT3'—SEQ ID NO:10) were synthesized and purified by Genemed Synthesis, Inc.

The total RNA of the honeybee venom gland was prepared as previously described (Chomczynski, et al, (1995) *Anal Biochem.* 225:163). Venom glands were collected from honeybee Apis mellifera by Apitronic Services (Richmond, British Columbia, Canada) and stored at −80° C. 100 venom glands in STAT-60 solution (TEL-TEST "B" Inc. TX) were homogenized using a glass-Teflon homogenizer. Total RNA was extracted and isolated using the RNA isolation kit from TEL-TEST "B" Inc.

The first strand cDNA was synthesized by reverse transcription using the total RNA from honey bee gland as the template and Oligo(dT) as the primer. The PX3.101 gene fragment was amplified by PCR using the degenerate PX3.101 primer and oligo(dT). The amplified DNA fragments were cloned into the NotI and BamHI sites of pBluescript sk(+) vector. The sequences of the DNA fragments were obtained through contracted service from Genemed Syntheses, Inc. The predicted protein sequences were analyzed to see if they matched peptide sequences obtained through protein sequencing: i.e., sequences: a) PSNEIFSR (SEQ ID NO:11) (residues 38 to 45 of SEQ ID NO:2), b) GFGGFGGLGGR (SEQ ID NO:12) (residues 24 to 34 of SEQ ID NO:2), c) VCVPR (SEQ ID NO:13) (residues 84 to 88 of SEQ ID NO:2), or d) PNVVPK (SEQ ID NO:14) (residues 55–60 of SEQ ID NO:2).

To get the full-length cDNA of PX3.101 gene including the coding sequence for the amino terminals and the signal peptide, 5'-RACE (Rapid Amplification of cDNA End) system (Gibco, MD) was used. Oligonucleotide primers ASEQ2 (5' ATCGCGGAACGCA 3'—SEQ ID NO:15) and ASEQ3 (5' AAGGATCCAAGTCTACATACAC 3'—SEQ ID NO:16) were synthesized and used to amplified the 5' end of PX3.101 cDNA. The PCR products were cloned into BamHI and SalI sites of pBluescript sk(+) vector and sequenced. The predicted protein sequences were analyzed to see if they matched the peptide sequence obtained through protein sequencing: GFGGFGGLGGR (SEQ ID NO:12) (residues 24 to 34 of SEQ ID NO:2). The protein and gene sequences of PX3.101 were analyzed by searching the database to identify any structural or functional motifs.

B. Results

A DNA fragment, containing coding sequence for peptides (NEIFSR (SEQ ID NO:10)—residues 40 to 45 of SEQ ID NO:2), (VCVPR (SEQ ID NO:13)—residues 84 to 88 of SEQ ID NO:2), and (PNVVPK (SEQ ID NO:14)—residues 55 to 60 of SEQ ID NO:2), was discovered. This DNA fragment is part of PX3.101 gene. The full-length PX3.101 gene (472 base pairs; SEQ ID NO:1) was isolated from the honeybee cDNA library. It contains a 276 base pair coding sequence (residues 74 to 349 of SEQ ID NO:1, a 5' end untranslated region, a 3' end untranslated region, and a poly(A) tail. The predicted PX3.101 protein consists of 92 amino acids (SEQ ID NO:2), including peptide (GFGGFGGLGGR (SEQ ID NO:12)—residues 24 to 34 of SEQ ID NO:2). The nucleotide and predicted amino acid sequence of PX3.101 are shown in FIG. 3A.

Like other secreted molecules, PX3.101 protein consists of a 19 amino acid signal peptide at the N-terminus (FIG. 3B; residues 1–19 of SEQ ID NO:2). The coding sequence for the PX3.101 signal peptide can be used to construct expression vector, to express recombinant proteins in secreted form.

The secreted and natural PX3.101 protein in honeybee venom starts with five GGX repeats (FIG. 3B; residues 20 to 34 of SEQ ID NO:2). GGX repeats are present in several structure proteins, including keratin (CAA28991), abducin (2739489), fibrillarin (P22232), elastin (207462), spider silk protein (AAC38847), precollagen D (2772914) and precollagen P (2388676) of mussel byssus, homeotic protein Spalt-accessory (AAC38847), putative immediate early protein of Alcelaphine herpesvirus 1 (2338034), EBNA-1 of Epstein-Barr virus (P0321 1), and many Mycobacterium tuberculosis proteins (CAA17751, CAA15537, CAA17576, CAA17749). GGX repeats form a condensed helical structure and may be involved in formation of polymers. Interestingly, auto-antibodies against keratin, fibrillarin or elastin are found in rheumatoid arthritis patients.

The C-terminus of PX3.101 is cysteine rich (FIG. 3B; residues 35–92 of SEQ ID NO:2. In 58 amino acids, there are 10 cysteines. A cysteine-rich motif such as this is present in a group of proteins, including tectorin (CAA68138), zonadhesin (3327421), IgG Fc binding protein (AAD15624), von Willebrand factor (CAA27765), ECM 18 (1100979), mucin (AF015521), hemocytin (P980920), SCO-spodin (CAA69868), tumor necrosis factor receptor II (2739045), a chymotrypsin inhibitor from honeybee (4699856), anti-coagulant protein C2 (1203803), and several proteins with similarity to EGF-like domain (CAA98455, AF016450, 1226303, U70857, 1226304).

Most of the proteins above are extracellular proteins mediating different signal transduction pathways and have more than one cysteine-rich motif. Tectorin, the protein associated with hearing disability, has three such cysteine-rich domains. IgG Fc binding protein has as many as twelve.

A database search identified several protein candidates as potential homologues of PX3.101. All of them are small proteins with a signal peptide and at least one cysteine-rich motif. Their schematic structures and name or accession number are included in FIG. 3C.

EXAMPLE IV

Expression and Purification of Recombinant PX3.101 Protein

A. Method

Figure 8:
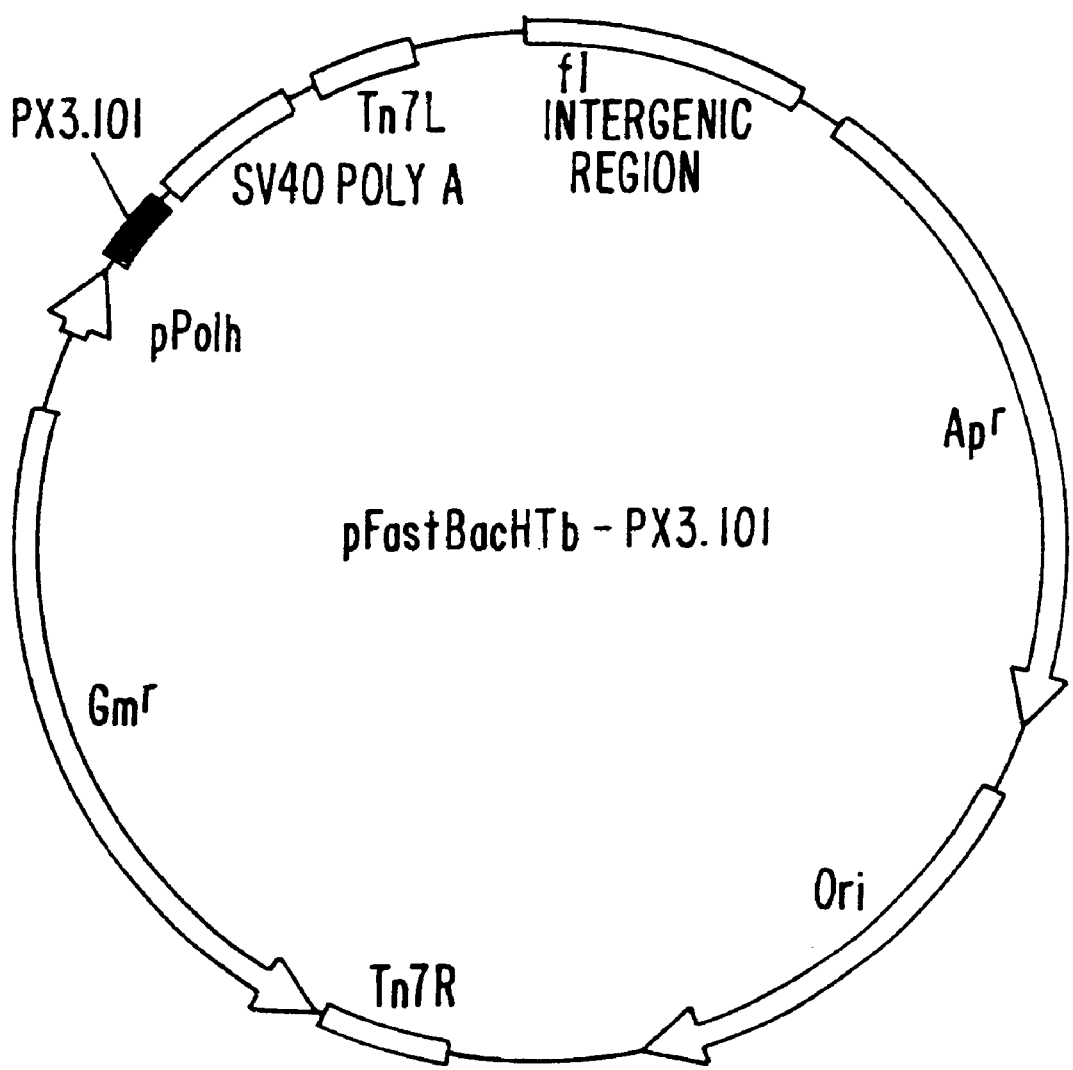
FIG. 8 is a schematic of the expression vector constructed to produce recombinant PX3.101 protein.

To generate the recombinant PX3.101 protein, the full-length cDNA of PX3.101 was cloned into pFastBacHTb, a baculovirus expression vector, in-frame with coding sequence for His-tag (Gibco, MD) (see FIG. 8). This virus expression vector was designed for high-level productions and rapid purification of the recombinant protein (Lukow, et al, Bio/Technology, 1989, 6:47).

pFastBacHTb-PX3.101 was used to transform DH10Bac cells (Gibco) for transposition into the bacmid. The recombinant bacid containing PX3.101 cDNA was isolated and assessed by PCR. To generate the baculovirus, SF9 cells (Invitrogen, Calif.) were infected with the recombinant bacmid. Following 5 days of incubation at 30° C., the virus stock was collected and used to infect SF9 cells to generate high titer virus stock. The titer of virus stock was determined by plaque assay.

To optimize the condition to generate PX3.101 protein, the recombinant baculovirus stock was used to infect High Five cells (Invitrogen, Calif.) an insect cell line generally expressing significantly higher levels of recombinant proteins compared to other insect cells (Wickham, et al, *Biotechnol. Prog.*, 1992, 8:391). High-five cells in mid-log phase of growth in one liter of serum-free medium were infected with the recombinant baculovirus stock (1:100 v/v). After incubation at 30° C. for 96 hrs, cells were harvested by centrifugation and lysed using guanidinium lysis buffer (6M guanidine hydrochloride, 20 mM sodium phosphate, 500 mM sodium chloride, pH 7.8).

After centrifugation, the supernatant was collected and incubated with pre-equilibrated PROBOND resin (Invitrogen, Calif.) at 4° C. for 3 hours. The column was washed sequentially with two bed volumes of the following buffers twice: denaturing binding buffer (8 M urea, 20 mM sodium phosphate, 500 mM sodium chloride, pH 7.8), denaturing wash buffer 1 (8 M urea, 20 mM sodium phosphate, 500 mM sodium chloride, pH 6.0), and denaturing wash buffer 2 (8 M urea, 20 mM sodium phosphate, 500 mM sodium chloride, pH 5.3). Recombinant PX3.101 was eluted from the column using denaturing elution buffer (8 M urea, 20 mM sodium phosphate, 500 mM sodium chloride, pH 4.0). The His tag was removed by rTEV protease digestion.

B. Results

Recombinant PX3.101 is expressed and soluble in denaturing lysis buffer. After removal of His tag by protease rTEV digestion, recombinant PX3.101 is almost identical in size on SDS-polyacrylamide gel electrophoresis. Recombinant PX3.101 was purified using PROBOND affinity column followed by HPLC. About 20 mg PX3.101 protein was obtained from 1 liter of cell culture.

Figure 7A:
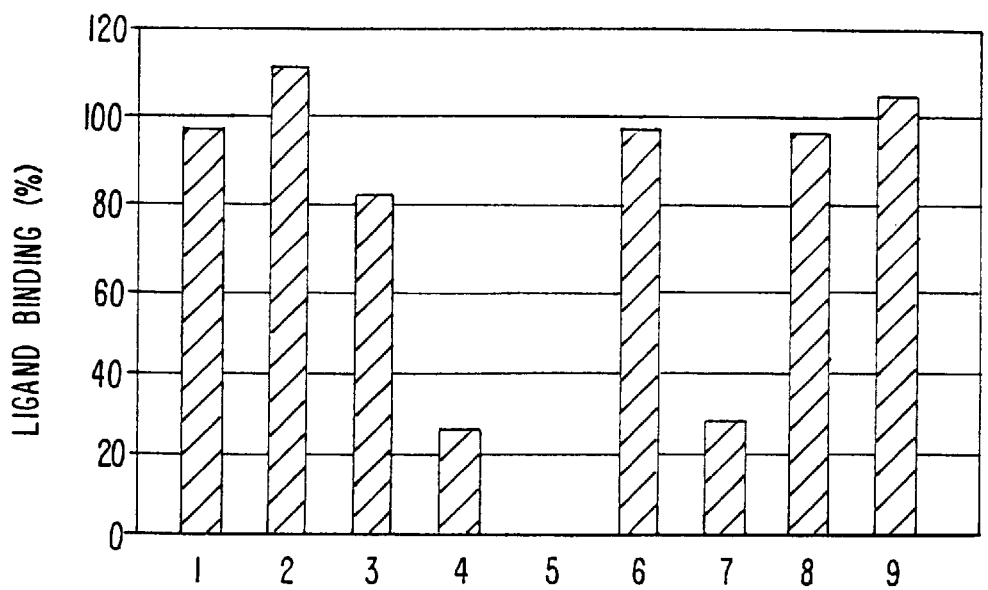
FIG. 7A is a chart showing inhibition of binding between the chemokine IL-8 with its receptor CXCR2 at different concentrations of PX3.101 purified from honeybee venom. Purified PX3.101 was added to 0.2 ml reaction solution to give final PX3.101 concentrations of 0, 0.01, 0.1, 1.0 and 10 μM (Columns 1 through 5, respectively). Reaction mixtures also contained 0.15 mg/ml membrane preparation of human recombinant CHO cells expressing CXCR2, 0.015 nM $^{125}$I IL-8, and 10 nM unlabeled IL-8, and were incubated for 60 minutes at room temperature. Bound radioligand was separated from unbound radioligand and the radioactivity counted on a gamma counter. The ligand bound was normalized and calculated as a percentage of the ligand bound in solutions without PX3.101. The effects of the purified PX3.101 on the binding of IL-8 to the receptor CXCR1 (Columns 6:0 μM; and column 7:10 μM)and of TNF-α (tumor necrosis factor -α) to TNF-α receptor are also shown (Column 8:0 μM; and column 9:10 μM). Details concerning the assay methods are described in Example VI. The results represent the averages of two measurements.
Figure 7B:
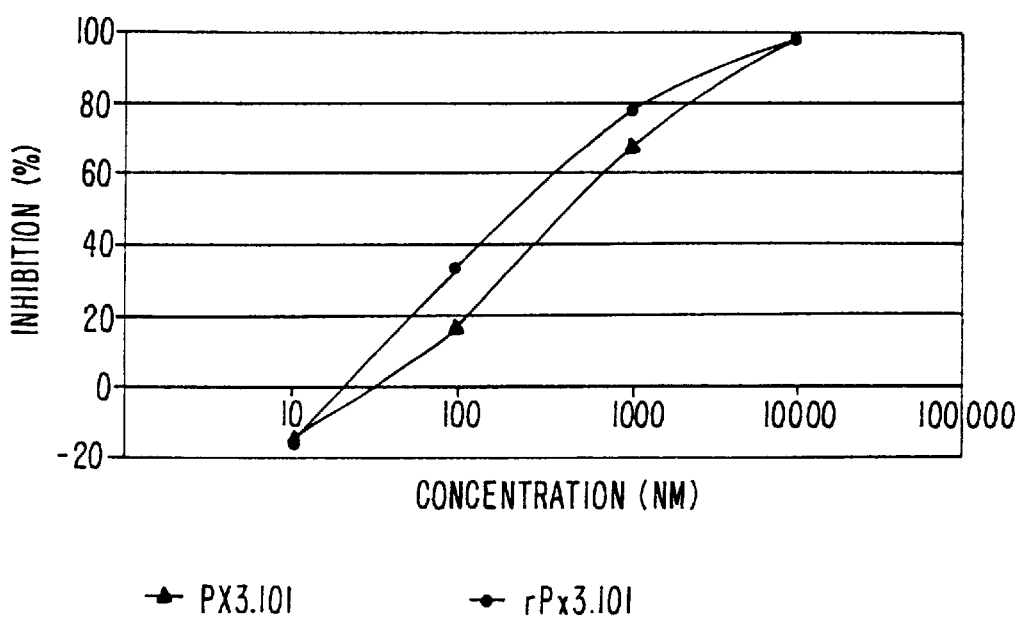
FIG. 7B shows inhibition plots demonstrating inhibition of IL-8/CXCR2 interaction by recombinant PX3.101 protein (●) and native PX3.101 protein from honeybee venom (▲).

After protein refolding, recombinant PX3.101 protein (●) and natural PX3.101 protein (▲) show equivalent activities in inhibiting the binding of IL-8 to its receptor CXCR2 (FIG. 7B).

EXAMPLE V

Animal Studies—Collagen Induced Arthritis Mouse Studies

A. General Method

The collagen-Induced Arthritis (CIA) animal model is widely acknowledged as the most appropriate in vivo model system to test potential therapeutics to treat rheumatoid arthritis and is recommended by the Food and Drug Administration for pre-clinical testing in preparation for an IND (Investigational New Drug) filing.

The following two animal studies began with 8–10 week old DBA/1J male mice from Jackson Laboratories (Bar Harbor, Me.). Disease was induced in all animals following the protocol described by Rosloniec, et al. (*Current Protocols in Immunology,* John Wiley & Sons, Inc. 1996). In brief, chicken collagen type II was dissolved in 10 mM acetic acid at 4 mg/ml and stirred overnight at 4° C. It is important that native collagen type II be kept cold while being dissolved to prevent its denaturation. Using a high-speed homogenizer, chicken type II collagen was emulsified in an equal volume of Complete Freund's Adjuvant (CFA) just prior to immunization. The solution is kept cold throughout the emulsification.

On Day 1, DBA/1JLacJ mice were injected interdermally at the base of the tail with 0.1 mg of the chicken collagen Type II emulsified in CFA. On Day 21, a second identical injection was administrated.

As set forth below, various treatments were administered subcutaneously, at various times into tissue of the upper back/shoulder area. Inflammation was recorded throughout each study, at least twice weekly, by counting the number of swollen toes, paws and ankles of each animal. Each joint was assigned a score of either 0 (no inflammation) or 1 (inflammation). According to this scoring system, a maximum score of 28 (7 measurements per limb×4 limbs) and a minimum score of 0 could be assigned to an animal at any single scoring occasion. This number, is representative of the disease Severity.

B. Study 1

1. Method

Five groups of 10 mice each were treated as follows:

Group 1: PX3.101 (200 µg/kg) administered subcutaneously for 15 days starting on Day 6.

Group 2: Bee Venom (1000 µg/kg) (obtained from Apitronic Services and dissolved in PBS administered subcutaneously for 30 days starting on Day 1.

Group 3: Negative Control (Phosphate Buffered in normal Saline (PBS) administered subcutaneously for 30 days starting on Day 1).

Group 4: INDOMETHACIN (positive control; available from Sigma Chemical Co., St. Louis, Mo.) administered orally for 30 days starting on Day 1 (1000 µg/kg).

Group 5: Normal Control (same as Group #3, except mice received no collagen).

On Day 52, blood samples were obtained from the Negative Control (Group #3) and PX3.101 treated animals (Group #1) to evaluate the immunogenicity of PX3.101 in this animal model. Serum was prepared and tested by Western Blot analysis as described in Example I.

2. Results

Figure 4:
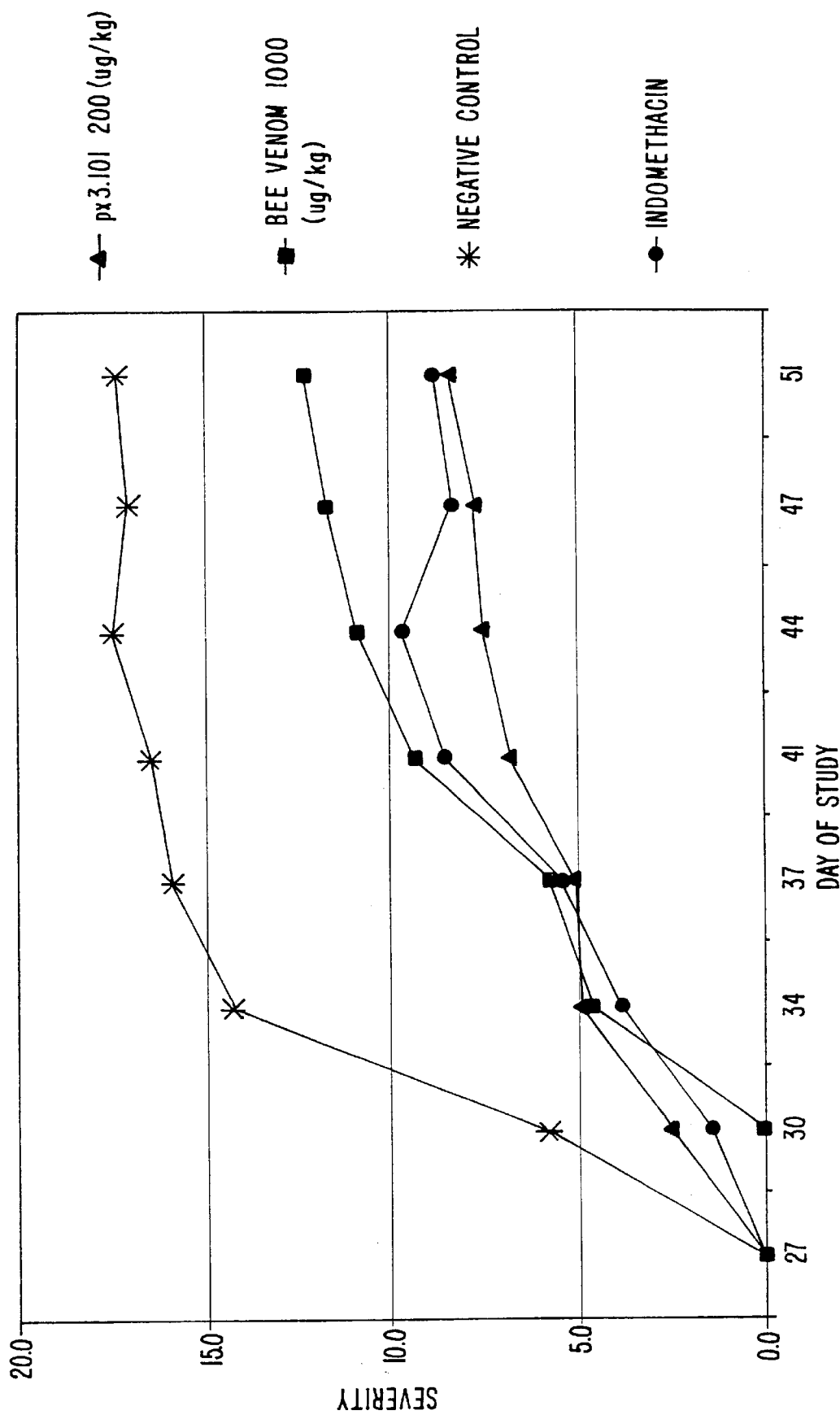
FIG. 4 is a chart showing the effectiveness of PX3.101 in controlling inflammation in the CIA (collagen-induced arthritis) mouse animal model. Indomethacin and bee venom serve as positive controls. PBS serves as the negative control. Severity is a measure of the degree of inflammation measured in each treatment group (see Example V for details).

Daily treatment of mice with PX3.101 at the does of 200 µg/kg from Day 16 to Day 30 (Group #3) suppressed inflammation in CIA (collagen-induced arthritis) mice. Its activity was comparable to INDOMETHACIN, a known anti-arthritic drug (daily treatment at a does of 1 mg/kg, Group #4) (see FIG. 4A). Statistical significance when compared to the Negative Control Group #3 is p <0.05.

Figure 5A:
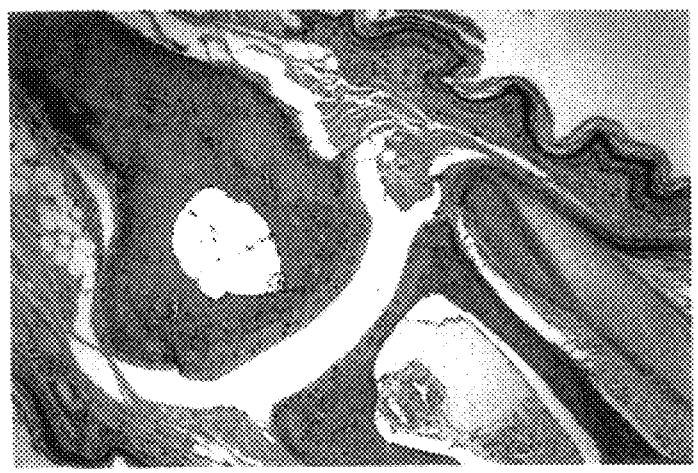
FIG. 5A (normal control) shows a joint for a mouse that was not injected with collagen to induce rheumatoid arthritis but which was injected with phosphate buffer in normal saline (PBS).
Figure 5B:
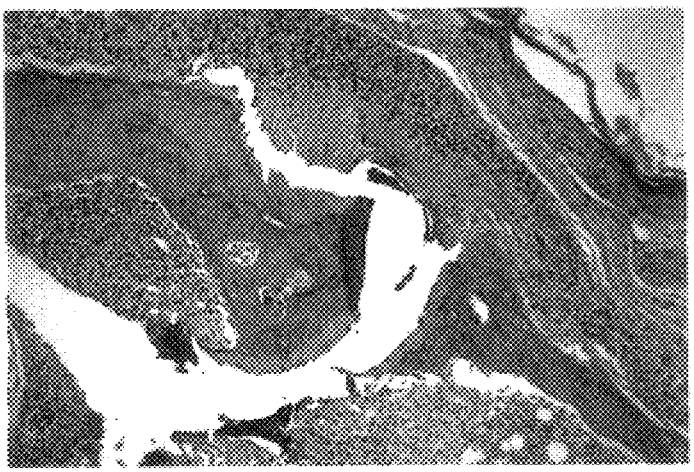
FIG. 5B (negative control) is a photograph of the joint of a mouse which was injected with collagen to induce rheumatoid arthritis and also injected with PBS.
Figure 5C:
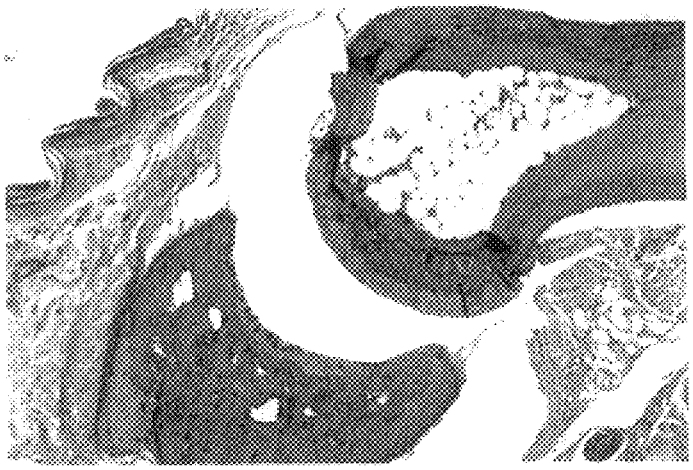
FIG. 5C is a photograph of the joint of a mouse which was injected with collagen to induce rheumatoid arthritis and also injected with a solution containing PX3.101 (200 μg/kg). Additional details are provided in Example V.

Histopathologic studies of joints from the mice treated with PX3.101 and PBS farther demonstrated the therapeutic activity of PX3.101 in suppressing inflammation (see FIGS. 5A–5C). In FIGS. 5A–5C, the white space located near the center of the photographs is a space between the bones (large dark regions) in a joint of the mouse that contains synovial fluid. The small dark spots or granules, particularly noticeable in FIG. 5B, are the nuclei of leukocytes (e.g., neutrophils, T-cells, macrophages, and other cells stimulated as part of an immune response) that have infiltrated the joint. These leukocytes actively degrade bone.

FIG. 5A shows a normal joint wherein collagen has not been injected to induce arthritis (Group 5). The dark bony material is smooth and undegraded and there are very few leukocytes present. In sharp contrast, many leukocytes were present in the joint from mice which were injected with collagen and then treated with PBS (Group 3, see FIG. 5B). In this negative control treatment group, bone erosion and penetration by leukocytes was observed and cartilage damage was obvious (see FIG. 5B). FIG. 5C is a photograph of a joint from a mouse from Group 1 that was treated with PX3.101. Very little bone erosion and cartilage damage was observed. There are also very few leukocytes present in the joint. This result suggests that PX3.101 can inhibit migration of leukocytes to inflammatory sites. The hypothesis is supported by our findings that PX3.101 inhibits the interaction between chemokine IL-8 and its receptor CXCR1 and CXCR2 (see FIG. 7A and Example VI). IL-8 is the major chemokine involved in inflammation. Its function includes recruiting neutrophils to the inflammatory site and activating them to release superoxide, proteases, and bioactive lipids.

Western Blot analysis did not detect antibodies against PX3.101 in the serum of mice treated with PX3.101 at 200 µg/kg for 15 consecutive days.

C. Study 2

1. Method

Four groups of 7–8 mice each were treated as follows:

Group 1: PX3.101 (200 µg/kg) administered subcutaneously for 15 days starting on Day 22.

Group 2: PX3.101 (40 µg/kg) administered subcutaneously for 15 days starting on Day 22.

Group 3: PX3.101 (8 µg/kg) administered subcutaneously for 15 days starting on Day 22.

Group 4: Negative Control (Phosphate Buffered in normal Saline (PBS) administered subcutaneously for 15 days starting on Day 22).

2. Results

Figure 6:
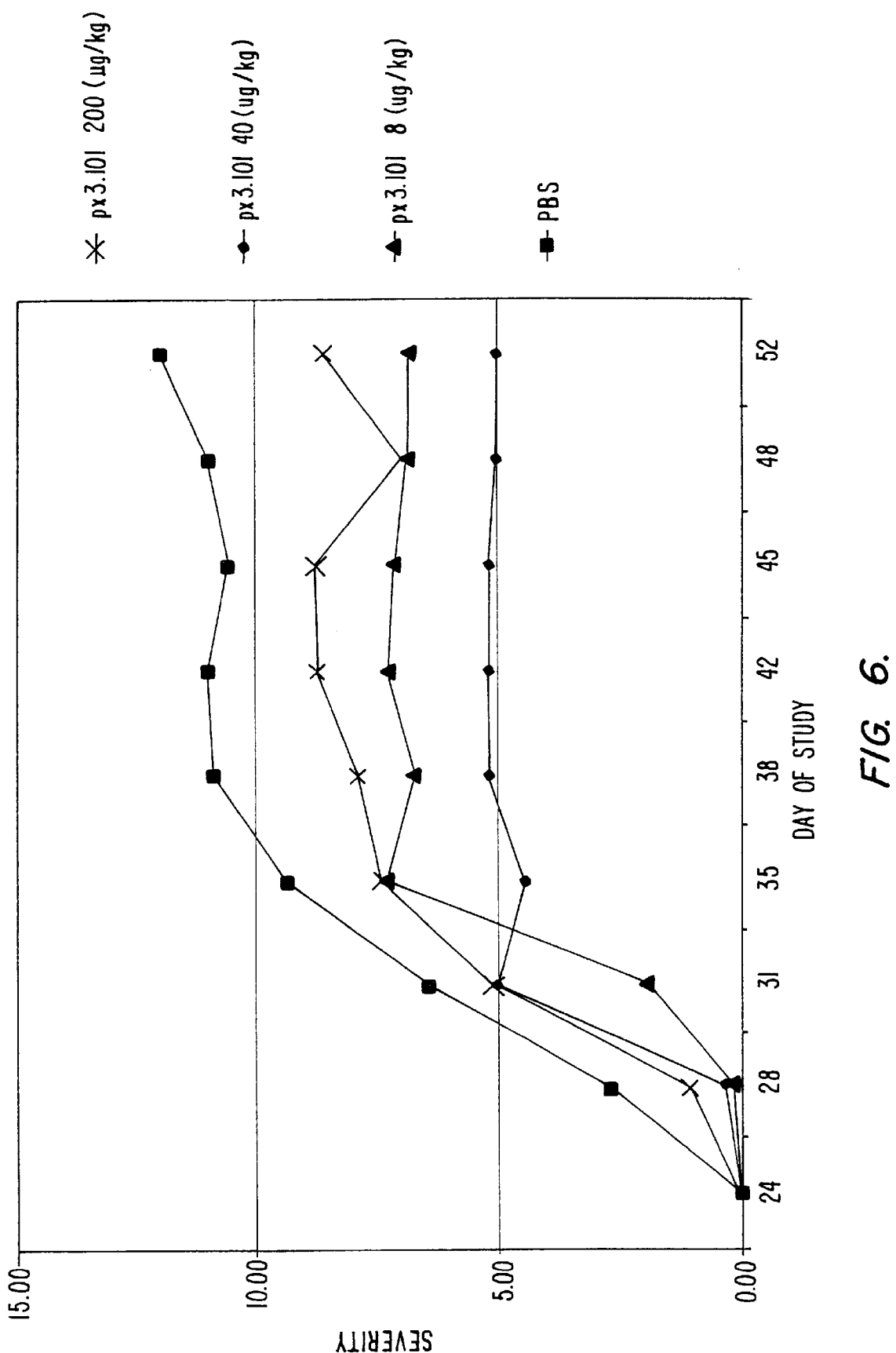
FIG. 6 is a chart showing the effectiveness of various concentrations of PX3.101 in controlling inflammation in the CIA (collagen-induced arthritis) mice model. Three doses of PX3.101 (8 μg/kg, 40 μg/kg, and 200 μg/kg) were tested. Severity is a measure of the degree of inflammation measured in each treatment group (see Example V for additional details).

The effectiveness of various concentrations of PX3.101 in suppressing inflammation in CIA (collagen-induced arthritis) was demonstrated. In this study, mice received PX3.101 treatment from Day 22 to Day 37, instead of Day 16 to Day 30 as in Study 1 above. Among three dosages (8 µg/kg, 40 µg/kg, and 200 µg/kg) tested, 40 µg/kg appears to be the optimal concentration (FIG. 6).

Results from this study indicate that the activities of PX3.101 molecule in this animal model depend on its dosage in a non-linear manner. Such phenomena have been observed in many cases in pre-clinical or clinical investigations, for example TNF-α soluble receptor and relaxin, a drug candidate in late stage clinical development for Scleroderma.

In addition, a substantial sustained therapeutic effect was observed after the treatment with PX3.101 was discontinued, suggesting possible long-lasting effect of this molecule.

D. Summary of Animal Studies

Therapeutic potential was demonstrated for a purified component from honeybee venom identified as PX3.101. In evaluating the data from the two studies, it appears that the in vivo activity of PX3.101 is dependent on its dosage and the time to start treatment. The most effective dosage of PX3.101 of the dosages tested was 40 µg/kg.

EXAMPLE VI

Mechanism of Action Studies

A. Method—Chemokine or Cytokine/Receptor Binding

Experiments to examine the effects of PX3.101 on chemokine or cytokine/receptor binding were carried out by Panlabs. For the inhibition of IL-8/CXCR2 binding, purified (naturally-occurring or recombinant) PX3.101 was added to 0.2 ml reaction solution that contained 0.15 mg/ml of a membrane preparation of human recombinant CHO cells expressing CXCR2, 0.015 nM $^{125}$I-labeled IL-8, and 10 nM unlabeled IL-8 to give a final PX3.101 concentration of 0, 0.01, 0.1, 1.0 and 10 µM. Reaction mixtures were incubated for 60 minutes at room temperature. Bound radioligand was then separated from unbound radioligand and the radioactivity measured on a gamma counter. Similar experiments were carried out to examine the effect of PX3.101 on IL-8/CXCR1 interaction, where the membrane preparation of human recombinant CHO cells that expressed CXCR1 was used and a single dose of PX3.101 (10 µM) was tested. TNF-α/TNF-α receptor binding experiments were carried out in a similar manner. Briefly, 10 µM PX3.101 was added to the reaction solution that contained 50 mM Tris-HCl (pH 7.4), 0.5 mM EDTA, 0.028 nM $^{125}$I-labeled TNF-α, 40 nM unlabeled TNF-α, and preparation of human U937 cells that expressed TNF-α receptor. The mixture was allowed to incubate for 3 hours at 4° C. Bound radioligands were separated from unbound and the radioactivity was counted on the gamma counter.

B. Results

PX3.101 was found to specifically inhibit the interaction between IL-8 and CXCR1 and the interaction between IL-8 and CXCR2 (FIG. 7A). PX3.101 inhibited IL-8 and CXCR2 interaction in a dose-dependent manner (FIG. 7A). Preliminary tests show an IC50 of 0.5 µM. However, the binding of TNF-a to its receptor was not affected by PX3.101 (FIG. 7A).

IL-8 is a major chemokine that regulates the inflammatory process. There is also research suggesting it may also be involved in tumor angiogenesis and tumor metastasis (Koch, et al., (1992) *Science* 258:1798). Since PX3.101 inhibits the binding of IL-8 to its receptors CXCR1 and CXCR2, PX3.101 is expected to be effective in the treatment of cancer, inflammatory diseases, autoimmune diseases and other diseases involving IL-8. Inhibition of the IL-8/CXCR2 interaction by purified naturally-occurring PX3.101 and recombinant PX3.101 is shown in FIG. 7B.

PX3.101 was also found to inhibit several enzymes involved in the pathogenesis of rheumatoid arthritis, including cyclooxygenases (COX 1 and COX2), phospholipase A2, phospholipase C, lipoxygenase, and the proteases trypsin and cathepsin G (data not shown). Several of these enzymes are either integrated in the phospholipid membrane (cyclooxygenases) or use fatty acids or phospholipids as their substrates (phospholipase A2, phospholipase C, lipoxygenase). Interestingly, PX3.101 inhibited COX1 when the enzyme purified in lipid vesicles was used but showed no inhibition to the free enzyme in solution. This result suggests that the inhibitions of the lipid/fatty acid related enzymes might occur through non-specific interaction between PX3.101 and lipids/fatty acids.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

TABLES

TABLE I

Selected fragments resulting from in-gel trypsin digestion

| Peptide Fragment | SEQ ID NO: | Amino Acid Sequence | MW (D) by Mass Spec |
|---|---|---|---|
| #47 | 17 | V-X-V-P-R | Not Determined |
| #62 | 18 | X-P-S-N-E-I-F-S-R | 1124.2 |
| #75 | 12 | G-F-G-G-F-G-G-L-G-G-R | 982.9 |
| #88 | 19 | X-X-P-N-V-V-P-K | Not Determined |

*V = Valine, P = Proline, C = Cysteine, K = Lysine, S = Serine, I = Isoleucine, E = Glutamic acid, N = Asparagine, X = Unsure

TABLE II

Figure 2C:
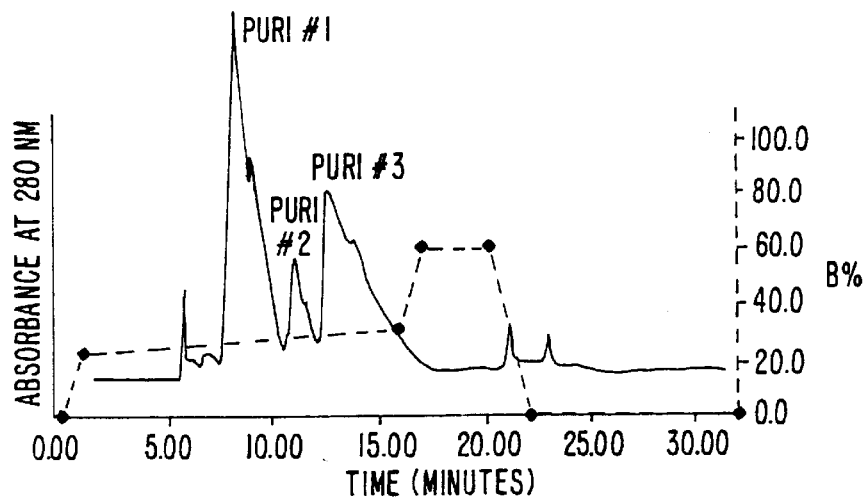
FIG. 2C is an example of the elution profile for the final purification step of PX3.101 using a second RP-HPLC column. PX3.101 fractions from the ion exchange HPLC purification shown in FIG. 2B were pooled and loaded onto another RP-HPLC column. Shown is the chromatography of the purification of PX3.101 from 2 g dry honeybee venom. PX3.101 fractions (Puri-#1, Puri-#2 and Puri-#3) are indicated on the profile. The mixture of Puri-1, Puri-2 and Puri -3 was used for animal studies and mechanism studies. The differences between PX3.101 fractions Puri-#1, Puri-#2 and Puri-93 are discussed in the text.

N-Terminal Sequences for PX3.101 protein fractions from honey bee venom (FIG. 2C)

| Name | SEQ ID NO: | N-terminal Sequence of PX3.101 proteins in honey bee venom | Measured MW (D) by mass spec | Predicted MW (D)* based on sequence |
|---|---|---|---|---|
| Puri-#1 | 20 | G-G-F-G-G-L-G-G-R-G | 7178 | 7178 |
| Puri-#2 | 21 | G-F-G-G-F-G-G-L-G-G | 7405 | 7382 |
| Puri-#3 | 22 | F-G-G-F-G-G-F-G-G-L | 7586 | 7586 |

*The molecular weights were predicted using IntelliGenetics program assuming that all the 10 cysteines form 5 pairs of disulfide bonds. It is also assumed that the C-terminus of the protein is intact and that there are no post-translational modifications of the molecule.
G = Glycine, F = Phenylalanine, R = Arginine, L = Leucine,

What is claimed is:

1. An isolated nucleic acid molecule that comprises a polynucleotide sequence that encodes a polypeptide having an amino acid sequence at least 75% identical to an amino acid sequence as set forth in SEQ ID NO:2 over a region at least about 40 amino acids in length when compared using the BLASTP algorithm with a wordlength (W) of 3, and the BLOSUM62 scoring matrix, wherein the polypeptide is effective to reduce the symptoms of an inflammatory disease.

2. The nucleic acid of claim 1, wherein the polynucleotide sequence encodes a polypeptide having an amino acid sequence as shown in SEQ ID NO:2.

3. An isolated nucleic acid molecule that comprises a polynucleotide sequence at least 75% identical to a nucleic acid sequence set forth in nucleotides 74 to 349 of SEQ ID NO:1 over a region of at least 50 nucleotides in length when compared using the BLASTN algorithm with a wordlength (W) of 11, M=5, and N=−4 and encodes a polypeptide that is effective in reducing the symptoms of an inflammatory disease.

4. The nucleic acid of claim 3, wherein the inflammatory disease is rheumatoid arthritis.

5. The nucleic acid of claim 1, wherein the polynucleotide sequence hybridizes to a nucleic acid having a sequence as set forth in residues 74 to 349 of SEQ ID NO:1 under stringent conditions, wherein the stringent conditions are conditions in which the ionic strength is equivalent to a solution containing 0.01 to 0.1M sodium ion, the pH is pH 7.0 to 8.3 and the temperature is at least 30° C. for polynucleotides 10 to 50 nucleotides in length and at least 60° C. for polynucleotides greater than 50 nucleotides in length.

6. The nucleic acid of claim 1, wherein the polynucleotide sequence is as set forth in residues 74 to 349 of SEQ ID NO:1.

7. The nucleic acid of claim 1, wherein the polynucleotide sequence is one that can be amplified using the forward primer 5' AAGGATCCACAGTGCAACGTAAGTTC 3' (SEQ ID NO:3) and reverse primer 5' ACTGATAAAATAATAAC 3' (SEQ ID NO:5).

8. The nucleic acid of claim 1, wherein the polynucleotide sequence is as set forth in SEQ ID NO:1.

9. The nucleic acid of claim 1, wherein the polynucleotide sequence is derived from a sample from bee venom.

10. The nucleic acid of claim 1, further comprising a promoter sequence operably linked to the polynucleotide sequence.

11. A vector comprising a nucleic acid of claim 1.

12. The vector of claim 11, wherein said vector is a baculovirus.

13. A cell containing the vector of claim 11.

14. A cell comprising a recombinant expression cassette comprising a promoter operably linked to a polynucleotide sequence which is at least about 75% identical to residues 74 to 349 of the polynucleotide sequence as set forth in SEQ ID NO:1 over a region at least about 50 nucleotides in length when compared using the BLASTN algorithm with a wordlength (W) of 11, M=5, and N=−4 and which encodes a polypeptide that is effective in reducing the symptoms of an inflammatory disease.

15. The cell of claim 14, wherein the insect cell line is a High Five insect cell line.

16. The nucleic acid of claim 14, wherein the inflammatory disease is rheumatoid arthritis.

17. The cell of claim 13, wherein the polynucleotide hybridizes to a nucleic acid having a sequence as set forth in residues 74 to 349 of SEQ ID NO:1 under stringent conditions, wherein the stringent conditions are conditions in which the ionic strength is equivalent to a solution containing 0.01 to 0.1M sodium ion, the pH is pH 7.0 to 8.3 and the temperature is at least 30° C. for polynucleotides 10 to 50 nucleotides in length and at least 60° C. for polynucleotides greater than 50 nucleotides in length.

18. The cell of claim 13, wherein the polynucleotide sequence is as set forth in residues 74 to 349 of SEQ ID NO:1.

19. The cell of claim 13, wherein the cell is an insect cell line.

20. A method for producing a polypeptide, the method comprising the steps of:
   (a) culturing a host cell containing the nucleic acid of claim 1 under conditions suitable for the expression of the polypeptide; and
   (b) recovering the polypeptide from the host cell culture.

21. The nucleic acid of claim 1, wherein the inflammatory disease is rheumatoid arthritis.

22. An isolated nucleic acid molecule comprising a nucleotide sequence selected from the group consisting of
   (a) a deoxyribonucleotide sequence complementary to nucleotides 74 to 349 of SEQ ID NO:1;
   (b) a ribonucleotide sequence complementary to nucleotides 74 to 349 of SEQ ID NO:1;
   (c) a nucleotide sequence complementary to the deoxyribonucleotide sequence of (a) or to the ribonucleotide sequence of (b);
   (d) a nucleotide sequence of at least 23 consecutive nucleotides that hybridizes to nucleotides 74 to 349 of SEQ ID NO:1; and
   (e) a nucleotide sequence that hybridizes to a nucleotide sequence of (d).

23. A vector comprising the nucleic acid of claim 21.

24. A cell containing the vector of claim 23.

* * * * *